United States Patent
Hematti et al.

(10) Patent No.: US 11,760,975 B2
(45) Date of Patent: Sep. 19, 2023

(54) GENERATION OF THERAPEUTIC CELLS USING EXTRACELLULAR COMPONENTS OF TARGET ORGANS

(71) Applicant: Wisconsin Alumni Research Foundation, Madison, WI (US)

(72) Inventors: Peiman Hematti, Middleton, WI (US); Eric G. Schmuck, Sun Prairie, WI (US); John A. Kink, Madison, WI (US); Amish N. Raval, Middleton, WI (US)

(73) Assignee: Wisconsin Alumi Research Foundation, Madison, WI (US)

( * ) Notice: Subject to any disclaimer, the term of this patent is extended or adjusted under 35 U.S.C. 154(b) by 574 days.

(21) Appl. No.: 15/941,409

(22) Filed: Mar. 30, 2018

(65) Prior Publication Data

US 2018/0282698 A1 Oct. 4, 2018

(30) Foreign Application Priority Data

Mar. 31, 2017 (NL) .................................. 2018628

(51) Int. Cl.
| | | |
|---|---|---|
| *C12N 5/0786* | (2010.01) | |
| *A61K 35/17* | (2015.01) | |
| *A61K 9/00* | (2006.01) | |
| *A61P 9/10* | (2006.01) | |
| *A61K 47/46* | (2006.01) | |
| *A61K 35/15* | (2015.01) | |
| *A61K 35/28* | (2015.01) | |
| *A61K 35/33* | (2015.01) | |

(52) U.S. Cl.
CPC .......... *C12N 5/0645* (2013.01); *A61K 9/0014* (2013.01); *A61K 9/0019* (2013.01); *A61K 35/15* (2013.01); *A61K 35/17* (2013.01); *A61K 35/28* (2013.01); *A61K 35/33* (2013.01); *A61K 47/46* (2013.01); *A61P 9/10* (2018.01); *C12N 2500/84* (2013.01); *C12N 2502/1323* (2013.01); *C12N 2502/1358* (2013.01)

(58) Field of Classification Search
CPC combination set(s) only.
See application file for complete search history.

(56) References Cited

U.S. PATENT DOCUMENTS

| | | | |
|---|---|---|---|
| 8,647,678 B2 | 2/2014 | Hematti | |
| 8,802,144 B2 | 8/2014 | Schmuck | |
| 2011/0045071 A1 | 2/2011 | Hematti | |
| 2012/0183575 A1* | 7/2012 | Gabrielsson | A61P 37/06 424/204.1 |
| 2016/0082042 A1 | 3/2016 | Hematti | |
| 2016/0354447 A1 | 12/2016 | Schmuck | |
| 2017/0304368 A1* | 10/2017 | Marban | C12N 15/113 |
| 2019/0134090 A1 | 5/2019 | Hematti | |

FOREIGN PATENT DOCUMENTS

| | | |
|---|---|---|
| WO | 2015031376 | 3/2015 |
| WO | 2015189063 A1 | 12/2015 |

OTHER PUBLICATIONS

Wei et al., Frontiers in Pharmacology 2021, 11:590470 (Year: 2021).*
Marban et al. Basic Research in Cardiology 2022, 117:12 11-13 (Year: 2022).*
Martinez, F.O , et al. "Alternative activation of macrophages: an immunologic functional perspective" Annual review of Immunology 27 (2009): 451-483.
Mosser, D.M. et al. "Exploring the full spectrum of macrophage activation." Nature reviews immunology 8.12 (2008): 958.
Stout, R D., et al. "Macrophages sequentially change their functional phenotype in response to changes in microenvironmental influences." The Journal of Immunology 175.1 (2005): 342-349.
Pollard, J. W. "Trophic macrophages in development and disease." Nature reviews immunology 9.4 (2009): 259.
Danon, David, et al. "Treatment of human ulcers by application of macrophages prepared from a blood unit." Experimental gerontology 32.6 (1997): 633-641.
Zuloff-Shani, A., et al. "Macrophage suspensions prepared from a blood unit for treatment of refractory human ulcers." Transfusion and apheresis science 30.2 (2004): 163-167.
Dominici et al. Minimal criteria for defining multipotent mesenchymal stromal cells. The International Society for Cellular Therapy position statement, (2006), Cytotherapy, 8(4):315-317.
Stoorvogel, Willem, et al. "The biogenesis and functions of exosomes." Tiaffic 3.5 (2002): 321-330.
Raposo, G., et al. "B lymphocytes secrete antigen-presenting vesicles." Journal of Experimental Medicine 183.3 (1996): 1161-1172.
Go AS, et al. Heart disease and stroke statistics—2014 update: A report from the american heart association. Circulation. 2014;129:e28-e292.
Menasche P, Vanneaux V. Stem cells for the treatment of heart failure. Curr Res Transl Med. 2016;64:97-106.
Huang P, Tian X, Li Q, Yang Y. New strategies for improving stem cell therapy in ischemic heart disease. Heart Fail Rev. 2016;21:737-752.
Zwetsloot PP, et al. Cardiac stem cell treatment in myocardial infarction: A systematic review and meta-analysis of preclinical studies Circ Res. 2016;118:1223-1232.
Suzuki G. Translational research of adult stem cell therapy. World J Cardiol. 2015;7:707-718.
Raval AN. Therapeutic potential of adult progenitor cells in the management of chronic myocardial ischemia. American Journal of cardiovascular drugs : drugs, devices, and other interventions. 2008;8:315-326.
Raval AN, Kamp TJ, Hogle LF. Cellular therapies for heart disease: Unveiling the ethical and public policy challenges. Journal of molecular and cellular cardiology 2008;45:593-601.
Ibrahim AG, Cheng K, Marban E. Exosomes as critical agents of cardiac regeneration triggered by cell therapy. Stem Cell Reports. 2014;2:606-619.

(Continued)

*Primary Examiner* — James D Schultz
(74) *Attorney, Agent, or Firm* — McDonnell Boehnen Hulbert & Berghoff LLP

(57) ABSTRACT

The invention relates to an ex vivo generated population of tissue-specific anti-inflammatory macrophages and methods of making and using such macrophages.

12 Claims, 27 Drawing Sheets
(15 of 27 Drawing Sheet(s) Filed in Color)

(56) References Cited

OTHER PUBLICATIONS

Asimakopoulos F, et al. Macrophages in multiple myeloma: Emerging concepts and therapeutic implications. Leuk Lymphoma. 2013;54:2112-2121.
Bashir S, et al. Macrophage polarization: The link between inflammation and related diseases. Inflamm Res. 2016;65:1-11.
Bloom DD, et al. A Reproducible Immunopotency Assay to Measure Mesenchymal Stromal Cell Mediated T cell Suppression. Department Cytotherapy. Feb. 2015; 17(2): 140-151.
Chakravarty T, et al. Allogeneic heart stem cells to achieve myocardial regeneration (allstar) trial: Rationale & design. Cell transplantation. 2016.
De Silva R, et al. X-ray fused with magnetic resonance imaging (xfm) to target endomyocardial injections: Validation in a swine model of myocardial infarction. Circulation 2006; 114:2342-2350.
Fujiu K, et al. Cardioprotective function of cardiac macrophages. Cardiovascular research. 2014;102:232-239.
Hatt CR, et al. Mri-3d ultrasound-x-ray image fusion with electromagnetic tracking for transendocardial therapeutic injections: In-vitro validation and in-vivo feasibility. Comput Med Imaging Graph. 2013;37:162-173.
Humeres, Claudio, et al. "Cardiac fibroblast cytokine profiles induced by proinflammatory or profibrotic stimuli promote monocyte recruitment and modulate macrophage M1/M2 balance in vitro." Journal of molecular and cellular cardiology 101 (2016): 69-80.
International Search Report and Written Opinion for PCT/US2018/025371, dated Jun. 22, 2018, 18 pages.
Kim J, et al. Mesenchymal stem cell-educated macrophages: A novel type of alternatively activated macrophages. Experimental hematology. 2009;37:1445 1453.
Kishore R, et al. More than tiny sacks: Stem cell exosomes as cell-free modality for cardiac repair. Circ Res. 2016;118:330-343.
Kovacic JC, et al. Safety and efficacy of consecutive cycles of granulocyte-colony stimulating factor, and an intracoronary cd133+ cell infusion in patients with chronic refractory ischemic heart disease: The g-csf in angina patients with ihd to stimulate neovascularization (gain i) trial. American heart journal. 2008;156:954-963.
Lalit PA, et al. Lineage reprogramming of fibroblasts into proliferative induced cardiac progenitor cells by defined factors. Cell Stem Cell 2016;18:354-367.
Lian X, et al. Robust cardiomyocyte differentiation from human pluripotent stem cells via temporal modulation of canonical wnt signaling. Proceedings of the National Academy of Sciences of the United States of America. 2012;109: E1848-1857.
Losordo DW, et al. A randomized, controlled pilot study of autologous cd34+ cell therapy for critical limb ischemia. Circulation. Cardiovascular interventions 2012;5:821-830.
Losordo DW, et al. Intramyocardial transplantation of autologous cd34+ stem cells for intractable angina: A phase i/iia double-blind, randomized controlled trial. Circulation 2007;115:3165-3172.
Losordo DW, et al. Intramyocardial, autologous cd34+ cell therapy for refractory angina. Circulation research. 2011;109:428-436.
Mantovani, Alberto, et al. "The chemokine system in diverse forms of macrophage activation and polarization." Trends in immunology 25.12 (2004): 677-686.
Mosser, D.M. "The many faces of macrophage activation." Journal of leukocyte biology 73.2 (2003): 209-212.
Mozaffarian D, et al. Heart disease and stroke statistics—2016 update: A report from the american heart association. Circulation. 2016;133:e38-360 (in two parts due to file size).
Povsic TJ, et al. The renew trial: Efficacy and safety of intramyocardial autologous cd34(+) cell administration in patients with refractory angina. JACC. Cardiovascular interventions. 2016;9:1576-1585.
Prathipati P, et al. Stem cell-derived exosomes, autophagy, extracellular matrix turnover, and mimas in cardiac regeneration during stem cell therapy. Stem Cell Rev. 2016.
Raval AN, et al. Bilateral administralion of autologous cd133+ cells in ambulatory patients with refractory critical limb schemia: Lessons learned from a pilot randomized, double-blind, placebo-controlled trial. Cytotherapy. 2014;16:1720-1732.
Schmuck EG, et al. Cardiac fibroblast-derived 3d extracellular matrix seeded with mesenchymal stem cells as a novel device to transfer cells to the ischemic myocardium. Cardiovascular Engineering and Technology. 2014;5:119-131.
Schmuck EG, et al. Intravenous followed by x-ray fused with mri-guided transendocardial mesenchymal stem cell injection improves contractility reserve in a swine model of myocardial infarction. Journal of cardiovascular translational research. 2015;8:438-448.
Search Report and Written Opinion for NL 2018628, 12 pages, 2018.
Shiraishi, Manabu, et al. "Alternatively activated macrophages determine repair of the infarcted adult murine heart." The Journal of clinical investigation 126.6 (2016): 2151-2166.
Spinali, Keith, et al. "Novel Cardiac Fibroblast-Derived Extracellular Matrix Educates Monocytes Into Alternatively Activated Macrophages With Low Inflammatory Marker Expression." Journal of the American College of Cardiology 71.11 (2018): A800.
Tomkowiak MT, et al. Targeted transendocardial therapeutic delivery guided by mri-x-ray image fusion. Catheterization and cardiovascular interventions : official journal of the Society for Cardiac Angiography & Interventions. 2011;78:468-478.
Warrick JW, et al. High-content adhesion assay to address limited cell samples. Integr Biol (Camb). 2013;5:720-727.
Ye L, et al. Cardiac repair in a porcine model of acute myocardial infarction with human induced pluripotent stem cell-derived cardiovascular cells. Cell Stem Cell. 2014;15:750-761.
Zhang J, et al. Extracellular matrix promotes highly efficient cardiac differentiation of human pluripotent stem cells: The matrix sandwich method Circulation research 2012;111:1125-1136.
Zhang J, et al. Functional cardiomyocytes derived from human induced pluripotent stem cells. Circulation research. 2009;104:e30-41.
Mantovani et al., Trends in Immunology 23(11); 549-555 (2002).
Saha et al., J Immunol 194:3079-3087 (2015).
Roy et al., J. Immunol 10:100033 (2020).
Van der Merwe et al. "Immunomodulatory approaches to CNS injury: extracellular matrix and exosomes from extracellular matrix conditioned macrophages", Neural Regen. Res. 11(4): 554-556, (Apr. 2016).

\* cited by examiner

A

B

| Exosome Characterization | | | | |
|---|---|---|---|---|
| Sample | Concentration | Particle Diameter (mean) | RNA Concentration (ng/mL) | Protein Concentration (mg/mL) |
| 1 | 1.90E+10 | 161.1 | 14.3 | 0.19 |
| 2 | 9.60E+09 | 183.2 | 14.8 | 0.17 |
| 3 | 7.80E+10 | 158.4 | 13.8 | 0.17 |
| 4 | 1.10E+10 | 175.1 | 17 | 0.25 |
| 5 | 7.30E+09 | 184.1 | 13.7 | 0.18 |
| 6 | 2.00E+09 | 170 | 12.8 | 0.16 |
| 7 | 1.60E+11 | 174.5 | 15.8 | 0.23 |
| 8 | 3.00E+10 | 187.3 | 17.2 | 0.27 |
| 9 | 1.30E+10 | 178.6 | 21.9 | 0.26 |
| 10 | 6.10E+09 | 169.2 | 17.4 | 0.26 |
| 11 | 1.30E+10 | 175.4 | 12.8 | 0.17 |
| 12 | 6.60E+09 | 162.3 | 14.7 | 0.28 |
| 13 | 1.20E+10 | 156.3 | 16.8 | 0.19 |
| 14 | 8.00E+09 | 156.1 | 16.6 | 0.18 |
| 15 | 1.20E+10 | 152.3 | 17.6 | 0.18 |
| 16 | 8.60E+09 | 230.6 | 11.8 | 0.28 |
| 17 | 2.10E+10 | 167.6 | 20.7 | 0.1 |
| Average | 2.45E+10 | 1.73E+02 | 1.59E+01 | 2.07E-01 |

FIG. 17

| Pathway | p value | Genes | Pathway ID |
|---|---|---|---|
| L13a-mediated translational silencing of Ceruloplasmin expression | 2.03E-09 | EIF3A,EIF3B,EIF3C,EIF3D,EIF3I,PABPC1,RPL18A,RPL19,RPL27A,RPL31,RPL35,RPL39,RPL41,RPS16,RPS18,RPS23,RPS27,RPS3 | R-HSA-156827 |
| Eukaryotic Translation Initiation | 2.03E-09 | EIF3A,EIF3B,EIF3C,EIF3D,EIF3I,PABPC1,RPL18A,RPL19,RPL27A,RPL31,RPL35,RPL39,RPL41,RPS16,RPS18,RPS23,RPS27,RPS3 | R-HSA-72613 |
| Formation of a pool of free 40S subunits | 2.03E-09 | EIF3A,EIF3B,EIF3C,EIF3D,EIF3I,RPL18A,RPL19,RPL27A,RPL31,RPL35,RPL39,RPL41,RPS16,RPS18,RPS23,RPS27,RPS3 | R-HSA-72689 |
| Cap-dependent Translation Initiation | 2.03E-09 | EIF3A,EIF3B,EIF3C,EIF3D,EIF3I,PABPC1,RPL18A,RPL19,RPL27A,RPL31,RPL35,RPL39,RPL41,RPS16,RPS18,RPS23,RPS27,RPS3 | R-HSA-72737 |
| GTP hydrolysis and joining of the 60S ribosomal subunit | 6.39E-09 | EIF3A,EIF3B,EIF3C,EIF3D,EIF3I,RPL18A,RPL19,RPL27A,RPL31,RPL35,RPL39,RPL41,RPS16,RPS18,RPS23,RPS27,RPS3 | R-HSA-72706 |
| Influenza Life Cycle | 2.71E-08 | CANX,HSP90AA1,KPNB1,NUP153,POLR2J,RAN,RPL18A,RPL19,RPL27A,RPL31,RPL35,RPL39,RPL41,RPS16,RPS18,RPS23,RPS27,RPS3 | R-HSA-168255 |
| Influenza Infection | 8.01E-08 | CANX,HSP90AA1,KPNB1,NUP153,POLR2J,RAN,RPL18A,RPL19,RPL27A,RPL31,RPL35,RPL39,RPL41,RPS16,RPS18,RPS23,RPS27,RPS3 | R-HSA-168254 |
| Nonsense-Mediated Decay (NMD) | 4.63E-07 | PABPC1,PPP2R1A,PPP2R2A,RPL18A,RPL19,RPL27A,RPL31,RPL35,RPL39,RPL41,RPS16,RPS18,RPS23,RPS27,RPS3 | R-HSA-927802 |
| Nonsense Mediated Decay (NMD) enhanced by the Exon Junction Complex (EJC) | 4.63E-07 | PABPC1,PPP2R1A,PPP2R2A,RPL18A,RPL19,RPL27A,RPL31,RPL35,RPL39,RPL41,RPS16,RPS18,RPS23,RPS27,RPS3 | R-HSA-975957 |
| Translation initiation complex formation | 1.54983E-06 | EIF3A,EIF3B,EIF3C,EIF3D,EIF3I,PABPC1,RPS16,RPS18,RPS23,RPS27,RPS3 | R-HSA-72649 |

FIG. 17 CONTINUED

| Pathway | p value | Genes | Pathway ID |
|---|---|---|---|
| Activation of the mRNA upon binding of the cap-binding complex and eIFs, and subsequent binding to 43S | 1.69268 E-06 | EIF3A,EIF3B,EIF3C,EIF3D,EIF3I,PABPC1,RPS16,RP S18,RPS23,RPS27,RPS3 | R-HSA-72662 |
| Influenza Viral RNA Transcription and Replication | 2.41122 E-06 | HSP90AA1,NUP153,POLR2J,RPL18A,RPL19,RPL27A,RPL31,RPL35,RPL39,RPL 41,RPS16,RPS18,RPS23,RPS27,RPS3 | R-HSA-168273 |
| Nonsense Mediated Decay (NMD) independent of the Exon Junction Complex (EJC) | 2.41122 E-06 | PABPC1,RPL18A,RPL19,RPL27A,RPL31,RPL35,RPL39,RPL41,RPS16,RPS18,RP S23,RPS27,RPS3 | R-HSA-975956 |
| Formation of the ternary complex, and subsequently, the 43S complex | 4.13276 E-06 | EIF3A,EIF3B,EIF3C,EIF3D,EIF3I,RPS16,RPS18,RPS23,RPS27,RPS3 | R-HSA-72695 |
| Peptide chain elongation | 8.24073 E-06 | RPL18A,RPL19,RPL27A,RPL31,RPL35,RPL39,RPL41,RPS16,RPS18,RPS23,RPS 27,RPS3 | R-HSA-156902 |
| Viral mRNA Translation | 8.24073 E-06 | RPL18A,RPL19,RPL27A,RPL31,RPL35,RPL39,RPL41,RPS16,RPS18,RPS23,RPS 27,RPS3 | R-HSA-192823 |
| Eukaryotic Translation Elongation | 1.03789 E-05 | RPL18A,RPL19,RPL27A,RPL31,RPL35,RPL39,RPL41,RPS16,RPS18,RPS23,RPS 27,RPS3 | R-HSA-156842 |
| SRP-dependent cotranslational protein targeting to membrane | 1.03789 E-05 | DDOST,RPL18A,RPL19,RPL27A,RPL31,RPL35,RPL39,RPL41,RPS16,RPS18,RP S23,RPS27,RPS3 | R-HSA-1799339 |
| Selenocysteine synthesis | 1.03789 E-05 | RPL18A,RPL19,RPL27A,RPL31,RPL35,RPL39,RPL41,RPS16,RPS18,RPS23,RPS 27,RPS3 | R-HSA-2408557 |

FIG. 17 CONTINUED

| Pathway | p value | Genes | Pathway ID |
|---|---|---|---|
| Ribosomal scanning and start codon recognition | 1.03789 E-05 | EIF3A,EIF3B,EIF3C,EIF3D,EIF3I,RPS16,RPS18,RPS23,RPS27,RPS3 | R-HSA-72702 |
| Eukaryotic Translation Termination | 1.03789 E-05 | RPL18A,RPL19,RPL27A,RPL31,RPL35,RPL39,RPL41,RPS16,RPS18,RPS23,RPS27,RPS3 | R-HSA-72764 |
| Metabolism of proteins | 2.27827 E-05 | ACO2,ANKRD28,ARL2,CALM1,CAND1,CANX,CAPZA2,CHML,COPA,CREB3L2,CTSA,CUL4A,CUL4B,DDOST,EIF3A,EIF3B,EIF3C,EIF3D,EIF3I,EXOC3,EXOC5,EXTL3,FBN1,FOXK2,GANAB,IDE,IGFBP3,KDELR2,NUCB1,NUP153,NUS1,PABPC1,PDIA5,PSMB1,PSMD2,QSOX1,RAB2A,RAB35,RAB5C,RHOA,RPL18A,RPL19,RPL27A,RPL31,RPL35,RPL39,RPL41,RPS16,RPS18,RPS23,RPS27,RPS3,SAM M50,SEC24C,SERP1,SMC1A,STAT3,STT3A,TGFBI,TIMM50,TMED10,TRIM13,UBA6,UBE2D3,UCHL1,USP9X | R-HSA-392499 |
| Metabolism of RNA | 2.70722 E-05 | CNOT7,DDX1,DHX16,ELAVL1,HNRNPL,NUP153,PABPC1,POLR2J,PPP2R1A,PPP2R2A,PRPF8,PSMB1,PSMD2,RAN,RPL18A,RPL19,RPL27A,RPL31,RPL35,RPL39,RPL41,RPS16,RPS18,RPS23,RPS27,RPS3,SET,SF3B2,SF3B6,SRSF1,TNPO1,YWHAZ | R-HSA-8953854 |
| Infectious disease | 2.89684 E-05 | CALM1,CANX,HSP90AA1,HSP90AB1,KPNB1,NUP153,POLR2J,PPIA,PSMB1,PSMD2,RAN,RPL18A,RPL19,RPL27A,RPL31,RPL35,RPL39,RPL41,RPS16,RPS18,RPS23,RPS27,RPS3 | R-HSA-5663205 |
| Regulation of expression of SLITs and ROBOs | 3.54692 E-05 | PABPC1,PSMB1,PSMD2,RPL18A,RPL19,RPL27A,RPL31,RPL35,RPL39,RPL41,RPS16,RPS18,RPS23,RPS27,RPS3 | R-HSA-9010553 |
| Disease | 7.47466 E-05 | CALM1,CANX,CAST,EPM2A,FKBP1A,HSP90AA1,HSP90AB1,IQGAP1,KPNB1,KRAS,LRP5,MAPK1,MTR,NF1,NOTCH3,NUP153,PDPK1,POLR2J,PPIA,PPP2R1A,PSMB1,PSMD2,RAN,RPL18A,RPL19,RPL27A,RPL31,RPL35,RPL39,RPL41,RPS16,RPS18,RPS23,RPS27,RPS3,STAT3 | R-HSA-1643685 |
| Translation | 8.66638 E-05 | DDOST,EIF3A,EIF3B,EIF3C,EIF3D,EIF3I,PABPC1,RPL18A,RPL19,RPL27A,RPL31,RPL35,RPL39,RPL41,RPS16,RPS18,RPS23,RPS27,RPS3 | R-HSA-72766 |
| Selenoamino acid metabolism | 0.000104379 | RPL18A,RPL19,RPL27A,RPL31,RPL35,RPL39,RPL41,RPS16,RPS18,RPS23,RPS27,RPS3 | R-HSA-2408522 |

FIG. 17 CONTINUED

| Pathway | p value | Genes | Pathway ID |
|---|---|---|---|
| Signaling by ROBO receptors | 0.000134734 | PABPC1,PSMB1,PSMD2,RHOA,RPL18A,RPL19,RPL27A,RPL31,RPL35,RPL39,RPL41,RPS16,RPS18,RPS23,RPS27,RPS3 | R-HSA-376176 |
| Axon guidance | 0.000666207 | CFL1,COL6A3,DLG1,HSP90AA1,HSP90AB1,ITGAV,ITGB1,KRAS,MAPK1,PABPC1,PSMB1,PSMD2,RHOA,RPL18A,RPL19,RPL27A,RPL31,RPL35,RPL39,RPL41,RPS16,RPS18,RPS23,RPS27,RPS3 | R-HSA-422475 |
| Ribosome | 0.001388141 | RPL18A,RPL19,RPL27A,RPL31,RPL35,RPL39,RPL41,RPS16,RPS18,RPS23,RPS27,RPS3 | hsa03010 |
| Beta1 integrin cell surface interactions | 0.001505014 | CD81,COL1A1,COL6A3,FBN1,ITGA11,ITGAV,ITGB1,TGFBI | integrin1_pathway |
| Signaling events mediated by VEGFR1 and VEGFR2 | 0.002030879 | HSP90AA1,HSP90AB1,IQGAP1,ITGAV,MAPK1,MYOF,PDPK1,RHOA | vegfr1_2_pathway |
| Calcineurin activates NFAT | 0.002059944 | CALM1,FKBP1A,NFATC3,PPIA | R-HSA-2025928 |
| Thyroid hormone signaling pathway | 0.002641666 | ATP2A2,ITGAV,KRAS,MAPK1,MED13L,MED4,NCOA3,NOTCH3,PDPK1,PFKP | hsa04919 |
| RNA transport | 0.003382484 | EIF1,EIF3A,EIF3B,EIF3C,EIF3D,EIF3I,EIF4EBP2,KPNB1,NUP153,PABPC1,PABPC4,RAN | hsa03013 |
| Amino acid and derivative metabolism | 0.005328462 | BCKDK,GLS,MTR,ODC1,PSMB1,PSMD2,RPL18A,RPL19,RPL27A,RPL31,RPL35,RPL39,RPL41,RPS16,RPS18,RPS23,RPS27,RPS3 | R-HSA-71291 |
| ErbB1 downstream signaling | 0.006259632 | ATF2,IQGAP1,KRAS,MAPK1,PDPK1,PPP2R1A,PPP2R2A,STAT3,YWHAZ | erbb1_downstream_pathway |
| Adaptive Immune System | 0.006405079 | ANAPC5,AREL1,CALM1,CANX,CAPZA2,CD81,CDC16,CTSA,FKBP1A,HLA-B,ITGAV,ITGB1,KIF3A,KRAS,MKRN1,NFATC3,NPDC1,PDPK1,PPIA,PPP2R1A,PSMB1,PSMD2,RNF14,RNF213,SEC24C,UBA6,UBE2D3,YWHAZ | R-HSA-1280218 |
| Major pathway of rRNA processing in the nucleolus and cytosol | 0.006509475 | RPL18A,RPL19,RPL27A,RPL31,RPL35,RPL39,RPL41,RPS16,RPS18,RPS23,RPS27,RPS3 | R-HSA-6791226 |

FIG. 17 CONTINUED

| Pathway | p value | Genes | Pathway ID |
|---|---|---|---|
| rRNA processing in the nucleus and cytosol | 0.010443922 | RPL18A,RPL19,RPL27A,RPL31,RPL35,RPL39,RPL41,RPS16,RPS18,RPS23,RPS27,RPS3 | R-HSA-8868773 |
| Class I PI3K signaling events | 0.010928245 | ARF6,CYTH3,HSP90AA1,KRAS,PDPK1,RHOA | pi3kcipathway |
| Arf6 trafficking events | 0.011987278 | ARF6,EXOC3,EXOC5,ITGA11,ITGAV,ITGB1 | arf6_traffickingpathway |
| MicroRNAs in cancer | 0.014870052 | DNMT3A,GLS,KRAS,MAPK1,MIR145,MIR181B1,MIR210,MIR30C2,MIR30D,MIRLET7A2,MIRLET7E,NOTCH3,RHOA,STAT3,VIM | hsa05206 |
| rRNA processing | 0.015134623 | RPL18A,RPL19,RPL27A,RPL31,RPL35,RPL39,RPL41,RPS16,RPS18,RPS23,RPS27,RPS3 | R-HSA-72312 |
| Role of Calcineurin-dependent NFAT signaling in lymphocytes | 0.017353796 | CHP1,FKBP1A,KPNB1,NFATC3,RAN,YWHAZ | nfat_3pathway |
| Estrogen signaling pathway | 0.017370769 | ATF2,CALM1,CREB3L2,GNAS,HSP90AA1,HSP90AB1,KRAS,MAPK1 | hsa04915 |
| Human papillomavirus infection | 0.027054685 | COL1A1,COL6A3,CREB3L2,DLG1,GNAS,HES7,HLA-B,ITGA11,ITGAV,ITGB1,KRAS,MAPK1,NOTCH3,PPP2R1A,PPP2R2A | hsa05165 |
| Downstream signaling events of B Cell Receptor (BCR) | 0.031848226 | CALM1,FKBP1A,KRAS,NFATC3,PPIA,PSMB1,PSMD2 | R-HSA-1168372 |
| MicroRNA (miRNA) biogenesis | 0.031848226 | AGO1,AGO2,POLR2J,RAN | R-HSA-203927 |
| Plexin-D1 Signaling | 0.036956563 | ARF6,ITGA11,ITGAV,ITGB1 | plexind1_pathway |
| Regulation of mRNA stability by proteins that bind AU-rich elements | 0.043307244 | ELAVL1,PABPC1,PSMB1,PSMD2,SET,TNPO1,YWHAZ | R-HSA-450531 |

FIG. 17 CONTINUED

| Pathway | p value | Genes | Pathway ID |
|---|---|---|---|
| ALK1 pathway | 0.043334188 | ACVR1,FKBP1A | alk1_2pathway |
| Adrenergic signaling in cardiomyocytes | 0.046271545 | ATF2,ATP2A2,CALM1,CAMK2D,CREB3L2,GNAS,MAPK1,PPP2R1A,PPP2R2A | hsa04261 |
| eNOS activation | 0.047988969 | CALM1,HSP90AA1,ZDHHC21 | R-HSA-203615 |

GENERATION OF THERAPEUTIC CELLS USING EXTRACELLULAR COMPONENTS OF TARGET ORGANS

STATEMENT REGARDING FEDERALLY SPONSORED RESEARCH

This invention was made with government support under HHSN268201000010C awarded by the National Institutes of Health. The government has certain rights in the invention.

CROSS-REFERENCE TO RELATED APPLICATIONS

This application claims priority to Netherlands Patent Application No. 2018628, filed Mar. 31, 2017, which is incorporated herein by reference in its entirety.

BACKGROUND

Cardiovascular disease is the most common cause of death in the United States and developed world. The human heart suffers loss of viable tissue and contractile function following myocardial infarction (MI) and this leads to heart failure, recurrent hospitalization, arrhythmias and death. Ischemic heart failure affects ~5 million Americans and is the most common reason for hospitalization in the United States. Mortality is high in these patients and similar to that of advanced cancer. Standard therapy involves beta-adrenergic and angiotensin II inhibiting medication that block maladaptive neurohormonal pathways, but these drugs are only partially effective and are not universally tolerated. Left ventricular assist devices and heart transplant may be offered but device failure, stroke, infection, and organ shortages limit these approaches. Local administration of individual angiogenic and cardio-regenerative proteins such as VEGF or gene transcription factors resoundingly failed or created unanticipated toxicities in human cardiovascular disease trials, which have virtually halted further investigations using these approaches.

Unfortunately, the heart has limited intrinsic regenerative potential. Traditional cardio-regenerative efforts have focused on administering stem cells to replenish adult heart cells. A dizzying array of stem/progenitor cell candidates have been tested to replenish heart and vascular cells, but to date, human trials have been negative or have shown only modestly positive results. Despite two decades of investigation, there are still no Food and Drug Administration (FDA) approved cell based therapies.

It is widely understood that most inflammatory cells have deleterious effects in the late stages of cardiac ischemic injury. However, it is recently suggested that alternatively-activated (M2) macrophages have a beneficial role in late cardiac repair, albeit these M2 responses are blunted in nature.

Although various categories of classification have been proposed, macrophages are typically divided into classically-activated (M1) and alternatively-activated (M2) macrophages. (Martinez et al., Annu. Rev. Immunol. 27:451-483 (2009)). Generally, M1 macrophages are pro-inflammatory scavenger cells that are active at times of infection and tissue injury and exhibit potent anti-microbial properties, reminiscent of type 1 T-helper lymphocyte (Th1) responses. Markers of M1 macrophages include, but are not limited to, CD86 and HLA-DR. In contrast, M2 macrophages, also called alternatively-activated macrophages, are anti-inflammatory, pro-angiogenic, and pro-regenerative "healing" cells that promote type 2 T-helper lymphocyte (Th2)—like responses, secrete less pro-inflammatory cytokines, and assist resolution of inflammation by trophic factor synthesis and phagocytosis. (Mosser et al., Nature Rev. 8:958-969 (2008)). Markers of M2 macrophages include, but are not limited to, CD163, CD206 and PD-L1.

Macrophages can be polarized by their microenvironment to assume different phenotypes associated with different stages of inflammation and healing. (Stout et al., J. Immunol. 175:342-349 (2005)). Certain macrophages are indispensable for wound healing. They participate in the early stages of cell recruitment and of tissue defense, as well as the later stages of tissue homeostasis and repair. (Pollard, Nature Rev. 9:259-270 (2009)). Macrophages derived from peripheral blood monocytes have been used to treat refractory ulcers. (Danon et al., Exp. Gerontol. 32:633-641 (1997); Zuloff-Shani et al., Transfus. Apher. Sci. 30:163-167 (2004).)

SUMMARY OF THE INVENTION

In a first aspect, provided herein is a population of CD163 low, CD206 high, CD16 low, PD-L1 high, PD-L2 high, TGF-β high, TNF-α low, IL-6 high, IL-10 high, IL-1b high, and Serpine-1 high cardiac fibroblast exosome educated macrophages (CF-EEM).

In a second aspect, provided herein is a population of CD163 low, CD206 high, CD16 low, PD-L1 high, PD-L2 high, TGF-β high, TNF-α low, IL-6 high, IL-1b high, and Serpine-1 high bone marrow exosome educated macrophages (BM-EEM).

In a third aspect, provided herein is a method of treatment to alleviate a condition in a subject in need thereof, the method comprising the step of: administering to the subject a population of macrophages as described herein, wherein the condition is a disease or injury described herein. In some embodiments, the population of macrophages is administered by injection. In some embodiments, the population of macrophages is administered by topical application. In some embodiments, the condition is a cardiovascular disease. In some embodiments, the condition is ischemic heart failure.

In some embodiments, the macrophages are administered by injection with a pharmaceutically-acceptable carrier. In some embodiments, the carrier is an injectable cardiac fibroblast-derived extracellular matrix.

In a fourth aspect, provided herein is a composition comprising, a population of macrophages as described herein; and a pharmaceutically-acceptable carrier. In some embodiments, the carrier is selected from the group consisting of liquid, oil, lotion, salve, cream, foam, gel, paste, powder, film, and hydrogel. In some embodiments, the carrier is an injectable cardiac fibroblast-derived extracellular matrix (CF-ECM). In some embodiments, the CF-ECM additionally comprises cardiac fibroblast derived exosomes.

In a fifth aspect, provided herein is a method for generating an anti-inflammatory macrophage, the method comprising the step of: co-culturing a CD14+ cell with tissue-specific cells or tissue-specific extracellular factors in vitro until the CD14+ cell acquires an anti-inflammatory macrophage phenotype.

In some embodiments, the tissue-specific cells are cardiac fibroblasts. In some embodiments, the extracellular factor is specific to cardiac tissue.

In some embodiments, the extracellular factor is selected from the group consisting of exosomes, micro-vesicles and extracellular matrix.

In a sixth aspect, provided herein is a population of anti-inflammatory macrophages produced by the methods described herein.

In some embodiments, the CD14+ cell is a monocyte. In some embodiments, the tissue-specific cells are selected from the group consisting of bone marrow cells, skin cells, lung cells, pancreatic cells, liver cells, kidney cells, brain cells, endocrine cells, and cells from reproductive organs. In some embodiments, the tissue-specific extracellular factor is selected from the group consisting of exosomes, microvesicles, and extracellular matrix.

INCORPORATION BY REFERENCE

All publications, patents, and patent applications mentioned in this specification are herein incorporated by reference to the same extent as if each individual publication, patent, and patent application was specifically and individually indicated to be incorporated by reference.

BRIEF DESCRIPTION OF DRAWINGS

The patent or patent application file contains at least one drawing in color. Copies of this patent or patent application publication with color drawings will be provided by the Office upon request and payment of the necessary fee.

The invention will be better understood and features, aspects, and advantages other than those set forth above will become apparent when consideration is given to the following detailed description thereof. Such detailed description makes reference to the following drawings.

FIG. 17 shows cardiac fibroblast total RNA isolation. Exosomes from the cardiac fibroblasts were processed for total RNA isolation using the SeraMir Exosome RNA Purification Column kit (Cat #RA808A-1, System Biosciences, Palo Alto, Calif.) according to the manufacturer's instructions. For each sample, 1 µl of the final RNA eluate was used for measurement of small RNA concentration by Agilent Bioanalyzer Small RNA Assay using Bioanalyzer 2100 Expert instrument (Agilent Technologies, Santa Clara, Calif.). Cardiac fibroblast exosomes derived from three donors were compared by RNA sequencing for similarities. Briefly, the expected counts per gene were estimated in each sample using RSEM. The counts were filtered keeping only those genes that had at least one expected count (per gene) in all three samples. Next, the TMM (trimmed method of means) was computed to normalize the counts. The counts per million (CPM) computed and then the co-efficient of variation (CV=stdev/mean) was calculated for each gene across the three samples. Finally, a pathway enrichment analysis was carried out to determine how the genes that are highly conserved across the three samples would be expected to influence an effector cell. The results demonstrate the pathways and genes that are common and highly expressed in cardiac fibroblast exosomes.

DETAILED DESCRIPTION OF THE INVENTION

Figure 1:
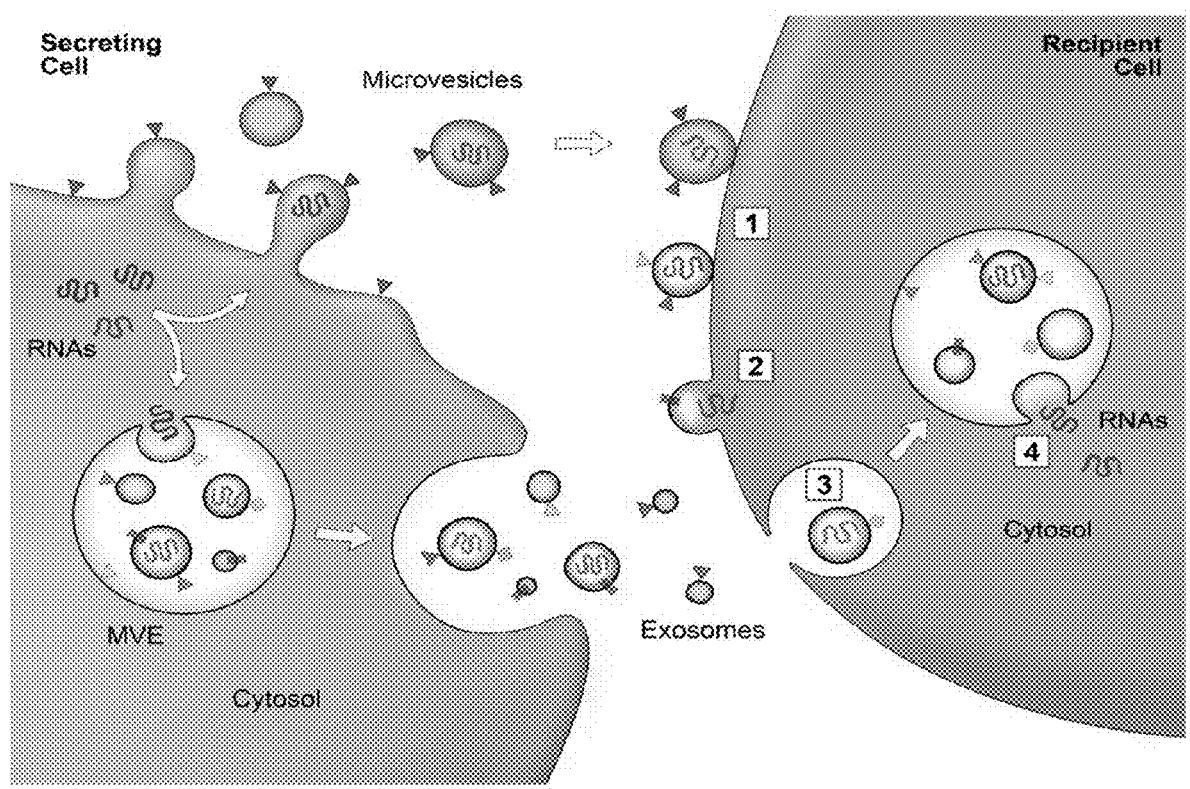
FIG. 1 is a diagram of the formation, release and uptake of various types of extracellular vesicles (EVs) from the secreting cell to the recipient cell. The larger microvesicles bud directly from the plasma membrane, whereas exosomes are smaller vesicles of different sizes which are first formed by the internalization of the cell membrane to produce endosomes. Subsequently, many small vesicles are formed inside the endosome by invagination of sections of the endosome membrane. Such endosomes are called multivesicular bodies (MVBs). Finally, the MVBs fuse with the cell membrane and release the intraluminal endosomal vesicles into the extracellular space to become exosomes. Proteins and various nucleic acids have recently been identified in the exosomal lumen, including mRNAs, microRNAs (miRNAs), and other non-coding RNAs (ncRNAs). These internal components can be taken up by neighboring cells or distant cells and modulate recipient cell phenotype and activity. Image source: Lieff, J. "Vesicle Transport Information," Searching for the Mind, Jan. 19, 2014, jonlieffmd.com.

The present disclosure broadly relates to an anti-inflammatory tissue-specific educated macrophage as well as methods for making and using such a macrophage.

In one aspect of the invention, CD14$^+$ monocytes or macrophages are co-cultured with tissue-specific cells or extracellular factors to yield tissue-specific educated macrophages. Educated macrophages generated by the methods of the present invention may be used to treat or prevent a disease by administration of the educated macrophages to a subject in need thereof.

As used herein, "educated macrophages" refers to tissue-specific anti-inflammatory and tissue reparative macrophages generated ex vivo by co-culturing a CD14$^+$ monocyte or macrophage with a tissue-specific cell or with an extracellular factor. Educated macrophages generated by co-culture of this type are generally characterized as CD163 low, CD206 high, CD16 low, PD-L1 high, PD-L2 high, TGF-β high, TNF-α low, and IL-1b high compared to non-educated macrophages. Levels of characteristic markers may be measured by flow cytometry, gene expression analysis, or other means known in the art. In one embodiment, the educated macrophages are specific to cardiac cells and are generated by co-culturing CD14$^+$ monocytes or macrophages with cardiac-specific cells or extracellular factors. In one embodiment, the educated macrophages are specific to bone marrow cells and are generated by co-culturing CD14$^+$ monocytes or macrophages with bone-marrow-specific cells or extracellular factors.

Co-Culture

CD14$^+$ cells are co-cultured with cells from a specific tissue ("tissue-specific cells") or with tissue-specific extracellular factors to yield educated macrophages. Methods of co-culturing CD14$^+$ cells with mesenchymal stem cells (MSCs) to generate MSC-educated macrophages (referred to herein as BM-MEM) have been described, see U.S. Pat. No. 8,647,678 and U.S. Patent Publication No. 2016/0082042, both incorporated herein by reference.

CD14$^+$ cells are co-cultured ex vivo with tissue-specific cells or tissue-specific extracellular factors in any culture medium known in the art suitable for survival and growth of the co-culture components. The co-cultures may be maintained for between 0-28 days to generate educated macrophages. Co-cultures may generate educated macrophages with the desired immuno-phenotype after 0, 1, 2, 3, 4, 5, 6, 7, 8, 9, 10, 11, 12, 13, 14, 15, 18, 20, 23, 25 or more than 26 days. In some embodiments, co-cultures yield educated macrophages after 10 days. In some embodiments, co-cultures yield educated macrophages after 5 days. In one embodiment, co-cultures yield educated macrophages after 1 day.

In some cases, tissue-specific cells or tissue-specific extracellular factors are subjected to additional purification steps prior to use in co-culture to obtain educated macrophages. Tissue-specific cells or extracellular factors can be added in a single dose or repeated doses to CD14$^+$ cultures to generate educated macrophages.

For co-cultures of the present invention, monocytes or macrophages can be co-cultured with tissue-specific cells or tissue-specific extracellular factors such that the cells are in direct physical contact. Alternatively, the co-culture components can be placed in sub-compartments that are in fluid communication but separated by a semi-permeable membrane. The semi-permeable membrane allows the exchange of soluble medium components and factors secreted by the cells but is impenetrable for the cells themselves. The pores within the semi-permeable membrane are sufficiently small to prevent cell penetration but large enough to allow soluble medium components to pass across the membrane, and are typically are between 0.1-1.0 μm, but other pore sizes can be suitable.

Various methods of cell separation and isolation are known in the art and can be used to separate the educated macrophages from the tissue-specific cells and tissue-specific extracellular factors depending on factors such as the desired purity of the isolated cell populations. For example, educated macrophages can be isolated from the co-culture using flow cytometry or magnetic based sorting. Educated macrophages can be maintained in culture in any medium that supports macrophages in vitro. Also, educated macrophages can be stored using methods known in the art including, but not limited to, refrigeration, cryopreservation, vitrification, lyophilization, and immortalization.

As used herein, "CD14$^+$ cell" refers to a monocyte or a macrophage. CD14$^+$ cells can be derived from any suitable source. The skilled artisan will appreciate the advantageous efficiency of generating macrophages from peripheral blood monocytes for co-cultures. Alternatively, macrophages can also be isolated from cellular outgrowth of a tissue sample taken from an individual. Peripheral blood monocytes can be cultured for various times and under various conditions before co-culture or can be added to the exosomes or extracellular matrix directly for co-cultures. In one embodiment, monocytes are harvested from a subject by leukapheresis. In one embodiment, CD14+ cells are isolated from peripheral blood. In one embodiment, CD14+ cells are isolated from peripheral blood of a patient who has first been treated with an agent including but not limited to G-CSF, GM-CSF, Mozobil™ (plerixafor injection) and the like to mobilize cells into the peripheral blood. In one embodiment, CD14+ cells are isolated from peripheral blood with G-CSF stimulation. In one embodiment CD14+ cells are isolated from bone marrow aspirates. In one embodiment CD14+ cells are isolated from tissues or organs such as heart. In one embodiment CD14+ cells are derived from pluripotent stem cells such as embryonic stem cells or induced pluripotent stem cells.

As used herein "macrophage" refers to a mononuclear phagocyte characterized by the expression of CD14 and lack of expression of dendritic or mesenchymal cell markers.

As used herein "mononuclear leukocytes" or "monocytes" are white blood cells that can differentiate into macrophages when recruited to tissues and can influence both innate and adaptive immune system.

As used herein, "high" means that the cells are characterized by higher expression of a particular cytokine compared to control macrophages cultured without tissue-specific cells or extracellular factors. For example, "IL-6 high" indicates that macrophages co-cultured with tissue-specific cells or extracellular factors express higher amounts of IL-6 than macrophages that have not been co-cultured with tissue-specific cells or extracellular factors. Similarly, "low" means that the cells are characterized by lower expression of a particular cytokine. For example, "IL-12 low" indicates that macrophages co-cultured with tissue-specific cells or extracellular factors express lower amounts of IL-12 than macrophages that have not been co-cultured with tissue-specific cells or extracellular factors. "Low" can also mean that the expression levels are below the detection limit.

Tissue-Specific Cells and Extracellular Factors

The skilled artisan will appreciate that monocytes, macrophages, tissue-specific cells, and extracellular factors employed in methods described herein can be cultured or co-cultured in any medium that supports their survival and growth. In one embodiment the medium is serum free-medium including but not limited to X-VIVO™ 15 and STEMPRO™ serum-free media. In one embodiment the medium uses human platelet lysates to replace the human AB serum in the macrophage medium. Co-cultures do not require the addition of cytokines. Tissue-specific cells, extracellular factors and macrophages can be autologous, syngeneic, allogeneic, or third party with respect to one another.

As used herein, "mesenchymal stem cells (MSC)" refers to the fibroblast-like cells that reside within virtually all tissues of a postnatal individual. An ordinarily skilled artisan will appreciate that the cells referred to herein as mesenchymal stem cells or MSCs are also known in the art as mesenchymal stromal cells, marrow stromal cells, multipotent stromal cells, and perhaps by other names. An MSC within the scope of this disclosure is any cell that can differentiate into osteoblasts, chondrocytes, and adipocytes. An MSC within the scope of this disclosure is positive for the expression of CD105, CD73, and CD90 while lacking expression of CD45, CD34, CD14 or CD11b, CD79α or CD19, and HLA-DR surface molecules. (Dominici et al. Minimal criteria for defining multipotent mesenchymal stromal cells. The International Society for Cellular Therapy position statement, (2006), Cytotherapy, 8(4):315-317). While these markers are known to characterize MSCs derived from most tissues, it is understood in the art that MSCs from some sources could exhibit differences in cell surface marker expression. Within bone marrow, MSCs provide the stromal support tissue for hematopoietic stem cells. MSCs can differentiate into cells of the mesenchymal lineage. In some embodiments, MSCs are co-cultured with CD14$^+$ cells to generate MSC educated macrophages (referred to herein as MEMs).

In some embodiments of the present invention the tissue-specific cells are bone marrow mesenchymal stem cells (referred to herein as BM-MSCs). BM-MSCs are co-cultured with CD14$^+$ cells to generate bone marrow specific educated macrophages (referred to herein as BM-MEM).

In some embodiments of the present invention the tissue-specific cells are cardiac fibroblast cells (referred to herein as CF). CF are co-cultured with CD14$^+$ cells to generate cardiac fibroblast educated macrophages (referred to herein as CF-EM).

CFs, MSCs, BM-MSCs, and other cells described herein for use in the methods or compositions of the present invention may be derived or isolated from any suitable source. In one embodiment, CFs are isolated from donor heart tissue. In one embodiment, CFs are biopsied from a patient with a disease or injury as described herein. In one embodiment, CFs are differentiated from embryonic or induced pluripotent stem cells. In one embodiment, MSCs are isolated from cardiac tissue. In one embodiment, MSCs are isolated from tissue such as bone marrow and lung tissue. In one embodiment, MSCs are differentiated from embryonic or induced pluripotent stem cells.

As used herein, "extracellular factors" refers to extracellular vesicles, exosomes, micro-vesicles, extracellular matrix compositions, isolated extracellular matrix components and fragments or derivatives thereof, exosomes purified from an extracellular matrix, and combinations thereof. Extracellular factors are used in co-culture with CD14$^+$ cells to educate macrophages in a tissue-specific manner. Tissue-specific extracellular factors are derived or isolated for a cell from a specific tissue of interest. As used herein, "extracellular vesicles" refers to both exosomes and micro-vesicles.

As used herein, "exosomes" refer to small lipid vesicles released by a variety of cell types. Exosomes are generated by inward- or reverse budding, resulting in particles that contain cytosol and exposed extracellular domains of certain membrane-associated proteins (Stoorvogel et al., *Traffic* 3:321-330 (2002)). Methods of preparing exosomes from cells are known in the art. See, for example, Raposo et al., *J. Exp. Med.* 183:1161 (1996). In one method, exosomes are recovered from conditioned culture medium by centrifugation. In some embodiments of the invention, exosomes are co-cultured with macrophages to generate tissue-specific educated macrophages with increased specificity for the tissues from which the exosomes were derived. Exosomes suited for use in the methods can be derived fresh or can be previously frozen aliquots kept as a composition, thawed, and added in a single dose or repeated doses to CD14$^+$ cultures to generate educated macrophages. In some embodiments, exosome preparations may also include micro-vesicles. Without wishing to be bound by any particular theory, it is understood that tissue-specific exosomes are known to express surface markers of their tissue of origin which may result in tissue-specific educated macrophages that are targeted to the tissue of origin. Exosomes from the tissue of interest, for example a damaged tissue targeted for repair, are likely to contain tissue-specific translational or post translational factors, internal nucleic acids, and proteins that are specific to tissue of interest and superior for repair of said tissue.

Exosomes can have, but are not limited to, a diameter of about 10-300 nm. In some embodiments, the exosomes can have, but are not limited to, a diameter between 20-250 nm, 30-200 nm or about 50-150 nm. Exosomes may be isolated or derived from any cell type that resides in the target tissue of interest which can be isolated and cultured for a period of time appropriate for the isolation of exosomes.

In one embodiment, the exosomes are derived from bone marrow mesenchymal stem cells. Exosomes derived from bone marrow MSCs are co-cultured with CD14$^+$ cells to generate bone marrow exosome-educated macrophages (referred to herein as BM-EEM). When comparing external surface markers of MEMs to BM-EEMs by flow cytometry the BM-EEMs are CD163 and CD16 low and CD206, PDL-1, and PDL-2 high. When comparing gene expression by qPCR BM-EEMs are TGF, TNF, and IL1b high and IL6, serpine and VEGF low compared to the MEMs.

In one embodiment, the exosomes are derived from cardiac fibroblasts (referred to herein as CF-EVs). CF-EVs are co-cultured with CD14$^+$ cells to generate cardiac fibroblast exosome-educated macrophages (referred to herein as CF-EEM).

When comparing external surface markers of MEMs to BM-EEMs by flow cytometry the BM-EEMs are CD163 and CD16 low and CD206, PDL-1, and PDL-2 high. When comparing gene expression by qPCR BM-EEMs are TGF, TNF, and IL1b high and IL6, serpine and VEGF low compared to the MEMs. Moreover there are distinctions between the expression profiles of the BM-EEMs and the CF-EEMs. Comparing the BM-EEM profile to CF-EEM profile by flow cytometry, CD206 is slightly lower, as is CD16 in the CF-EEMs, but both PD-L1 and PDL-2 are higher compared to the BM-EEMs. Slight differences are also seen in gene expression by qPCR, most notably in the expression of IL-6.

TABLE 1

Characteristic surface marker phenotypes and cytokine growth factor profiles of some embodiments of the educated macrophages described herein.

| Educated Macrophage | Surface marker phenotype | Cytokine, growth factor profile | As compared to |
| --- | --- | --- | --- |
| MEM | CD163 high, CD206 high, CD16 high | TGF-β low, TNF-α low, IL-6 very high, IL-10 low, IL-1b low, VEGF-A high, Serpine-1 high | Un-educated macrophages |
| BM-EEM | CD163 low, CD206 high, CD16 low, PD-L1 high, PD-L2 high | TGF-β high, TNF-α low IL-6 high, IL-1b high, Serpine-1 high | Un-educated macrophages |
| CF-EEM | CD163 low, CD206 high, CD16 low, PD-L1 very high, PD-L2 very high | TGF-β high, TNF-α low, IL-6 high, IL-10 high, IL-1b high, Serpine-1 high | Un-educated macrophages |
| CF-ECM-EM | CD206 very high | | Un-educated macrophages |
| BM-EEM | CD163 low, CD206 high, CD16 low, PD-L1 high, PD-L2 high | TGF-β high, TNF-α high, IL-6 low, IL-10 high, FGF-2 low, IL-1b high, VEGF-A low, VEGF-C low, Serpine-1 low | MEM |

In one embodiment, the exosomes may be embedded within a cardiac fibroblast-derived extracellular matrix (CF-ECM) for use in a co-culture with CD14$^+$ cells. In one embodiment, the embedded matrix is created by saturating CF-ECM with CF-exosomes and vacuum drying the combination material resulting in the deposition of exosomes in the CF-ECM. In another embodiment, CD14$^+$ cells are co-cultured with cardiac fibroblast extracellular matrix to generate cardiac fibroblast extracellular matrix educated macrophages (referred to herein as CF-ECM-EM). In another embodiment, CD14+ cells are co-cultured with exosomes isolated from a cardiac fibroblast extracellular matrix to generate cardiac fibroblast ECM exosome educated macrophages (CF-ECM-EM).

As used herein, "cardiac fibroblast-derived extracellular matrix (CF-ECM)" refers to a 3-dimensional matrix that is substantially similar to, but not necessarily identical to, the in vivo 3-dimensional extracellular matrix of cardiac fibroblasts unique to cardiac tissue that heals after myocardial disease or injury. Substantial similarity is based on the type and abundance of the structural proteins present in the ECM, as well as on the presence of characteristic matricellular proteins such as growth factors and cytokines. In some embodiments, the CF-ECM is an engineered CF-ECM as described in U.S. Pat. No. 8,802,144 and U.S. Patent Publication No. US 2016/0354447, both of which are incorporated herein by reference.

An engineered CF-ECM can include structural proteins fibronectin, collagen type I, collagen type III, and elastin, and other structural proteins. In some embodiments, an engineered CF-ECM includes the structural protein collagen type V. Preferably, fibronectin molecules make up from 60% to 90%, or from 70% to 90%, or from 80% to 90%, of the structural protein molecules present in the engineered CF-ECM.

Before it is fragmented or lyophilized, the engineered CF-ECM has a thickness of 20-500 μm. In some embodiments, the unfragmented CF-ECM has a thickness range of 30-200 μm or of 50-150 μm. In some embodiments, more than 80% of the structural protein molecules are fibronectin molecules.

Preferably, the structural proteins of the engineered CF-ECM are not chemically cross-linked.

In addition to the structural proteins, the CF-ECM may include one or more matricellular proteins, such as growth factors and cytokines, as well as other substances. Non-limiting examples of other proteins that may be found in the cardiac ECM include latent transforming growth factor beta 1 (LTGFβ-1), latent transforming growth factor beta 2 (LTGFβ-2), connective tissue growth factor (CTGF), secreted protein acidic and rich in cysteine (SPARC), versican core protein (VCAN), galectin 1, galectin 3, matrix gla protein (MGP), sulfated glycoprotein 1, protein-lysine 6-oxidase, and biglycan. In some embodiments, the ECM may optionally include one or more of transforming growth factor beta 1 (TGFβ-1), transforming growth factor beta 3 (TGFβ-3), epidermal growth factor-like protein 8, growth/differentiation factor 6, granulins, galectin 3 binding protein, nidogen 1, nidogen 2, decorin, prolargin, vascular endothelial growth factor D (VEGF-D), Von Willebrand factor A1, Von Willebrand factor A5 A, matrix metalloprotease 14, matrix metalloprotease 23, platelet factor 4, prothrombin, tumor necrosis factor ligand superfamily member 11, and glia derived nexin.

Optionally, the engineered CF-ECM is decellularized, and is substantially devoid of intact cardiac fibroblast cells. In some embodiments, the CF-ECM may be seeded using methods that are known in the art with one or more cells that are therapeutic for cardiac disease or injury. Examples of therapeutic cells types that could be used to seed the CF-ECM bioscaffold include without limitation CF, CD14+ monocytes, macrophages, MSCs, CF-EEMs, BM-EEMs, BM-MEM, CF-ECM-EMs or combinations thereof.

Methods of making the engineered CF-ECM and information about its structure and composition are disclosed in, for example, U.S. Pat. No. 8,802,144 and U.S. Patent Publication No. US 2016/0354447, both of which are incorporated herein by reference.

Treatment

According to the methods of the present invention, educated macrophages are administered to a subject in need of thereof. Subjects in need of treatment include those already having or diagnosed with a disease or injury as described herein or those who are at risk of developing a disease or injury as described herein.

A disease or injury of the present invention may include, but is not limited to, conditions associated with aberrant, uncontrolled, or inappropriate inflammation, cardiovascular disease, atherosclerosis, cytokine release syndrome (CRS), and other disorders associated with cytokine storm such as adult respiratory distress syndrome (ARDS), and severe acute respiratory syndrome (SARS). CRS is a rapid and massive release of cytokines into the bloodstream which can lead to high fevers and cardiac dysfunction, and is frequently observed following administration of immunotherapeutics (e.g., therapeutic mAb infusions) and following adoptive T-cell therapies (e.g., administration of T-cells engineered to express CARs). While immunosuppression can potentially reverse a cytokine storm and return cytokines to normal levels, it can limit the efficacy of the immunotherapy. Advantageously, the methods provided herein improve the chance for the subject to receive therapeutic benefit from an immunotherapy while minimizing the risk for life threatening complications of CRS and other cytokine-associated toxicities.

Cardiovascular disease may refer to, but is not limited to, coronary heart disease, heart failure associated conditions (such as ischemic cardiomyopathy and non-ischemic cardiomyopathies such as infiltrative cardiomyopathy, inflammatory cardiomyopathy, myocarditis, valvular cardiomyopathy), chronic ischemia with preserved ejection fraction (such as chronic angina due to atherosclerosis), recent myocardial infarction or recent myocardial ischemia such as acute coronary syndrome, arrhythmia associated conditions such as conduction disturbances and tachyarrhythmias.

In some embodiments, a disease or injury of the present invention includes disease or injury of the lung such as, but not limited to, chronic obstructive pulmonary disease (COPD), asthma, bronchiolitis obliterans, and the like. In some embodiments, a disease or injury of the present invention includes disease or injury of the vasculature such as, but not limited to, peripheral artery disease and the like. In some embodiments, a disease or injury of the present invention includes disease or injury of the bone marrow such as, but not limited to, graft vs. host disease, bone marrow failure, and the like. In some embodiments, a disease or injury of the present invention includes disease or injury of the skin such as, but not limited to, burns, trauma, ischemic ulcers, neuropathic ulcers, and the like. In some embodiments, a disease or injury of the present invention includes disease or injury of the pancreases such as, but not limited to, diabetes. In some embodiments, a disease or injury of the present invention includes disease or injury of the liver such as, but not limited to, cirrhosis, liver failure, and the like. In some embodiments, a disease or injury of the present invention includes disease or injury of the kidney such as, but not limited to, acute and chronic renal failure. In some embodiments, a disease or injury of the present invention includes disease or injury of the brain such as, but not limited to, stroke, neurodegeneration, neurodevelopmental diseases, and the like. In some embodiments, a disease or injury of the present invention includes disease or injury of the endocrine organs such as, but not limited to, hormone deficiency or endocrine organ inflammation. In some embodiments, a disease or injury of the present invention includes disease or injury of the reproductive organs such as, but not limited to, infertility, hormone imbalance, menopause, premature aging, and the like. In some embodiments, a disease or injury of the present invention includes aging or a disease or injury associated with the normal human aging process.

As used herein, the terms "treat" and "treating" can refer to both therapeutic and prophylactic or preventive measures, wherein the object is to prevent or slow down (lessen) an undesired physiological change or pathological disorder resulting from a disease or injury as described herein. For purposes of this invention, treating the disease or injury includes, without limitation, alleviating one or more clinical indications, decreasing inflammation, reducing the severity of one or more clinical indications of the disease or injury, diminishing the extent of the condition, stabilizing the subject's disease or injury (i.e., not worsening), delay or slowing, halting, or reversing the disease or injury and bringing about partial or complete remission of the disease or injury. Treating the disease or injury also includes prolonging survival by days, weeks, months, or years as compared to prognosis if treated according to standard medical practice not incorporating treatment with educated macrophages.

Subjects in need of treatment can include those already having or diagnosed with a disease or injury as described herein as well as those prone to, likely to develop, or suspected of having a disease or injury as described herein. Pre-treating or preventing a disease or injury according to a method of the present invention includes initiating the administration of a therapeutic (e.g., human educated macrophages) at a time prior to the appearance or existence of the disease or injury, or prior to the exposure of a subject to factors known to induce the disease or injury. Pre-treating the disorder is particularly applicable to subjects at risk of having or acquiring the disease injury. As used herein, the terms "prevent" and "preventing" refer to prophylactic or preventive measures intended to inhibit undesirable physiological changes or the development of a disorder or condition resulting in the disease or injury. In exemplary embodiments, preventing the disease or injury comprises initiating the administration of a therapeutic (e.g., educated macrophages) at a time prior to the appearance or existence of the disease or injury such that the disease or injury, or its symptoms, pathological features, consequences, or adverse effects do not occur. In such cases, a method of the invention for preventing the disease or injury comprises administering educated macrophages to a subject in need thereof prior to exposure of the subject to factors that influence the development of the disease or injury.

As used herein, the terms "subject" or "patient" are used interchangeably and can encompass any vertebrate including, without limitation, humans, mammals, reptiles, amphibians, and fish. However, advantageously, the subject or patient is a mammal such as a human, or a mammal such as a domesticated mammal, e.g., dog, cat, horse, and the like, or livestock, e.g., cow, sheep, pig, and the like. In exemplary embodiments, the subject is a human. As used herein, the phrase "in need thereof" indicates the state of the subject, wherein therapeutic or preventative measures are desirable. Such a state can include, but is not limited to, subjects having a disease or injury as described herein or a pathological symptom or feature associated with a disease or injury as described herein.

In some cases, a method of treating or preventing a disease or injury as described herein comprises administering a pharmaceutical composition comprising a therapeutically effective amount of educated macrophages as a therapeutic agent (i.e., for therapeutic applications). As used herein, the term "pharmaceutical composition" refers to a chemical or biological composition suitable for administration to a mammal. Examples of compositions appropriate for such therapeutic applications include preparations for parenteral, subcutaneous, transdermal, intradermal, intramuscular, intracoronarial, intramyocardial, intrapericardial, intraperitoneal, intravenous (e.g., injectable), intraparenchymal, intrathecal, or intratracheal administration, such as sterile suspensions, emulsions, and aerosols. Intratracheal administration can involve contacting or exposing lung tissue, e.g., pulmonary alveoli, to a pharmaceutical composition comprising a therapeutically effective amount of educated macrophages, alone or in combination with tissue-specific ECM or extracellular vesicles. In some cases, pharmaceutical compositions appropriate for therapeutic applications may be in admixture with one or more pharmaceutically-acceptable excipients, diluents, or carriers such as sterile water, physiological saline, glucose or the like. For example, educated macrophages described herein can be administered to a subject as a pharmaceutical composition comprising a carrier solution.

Formulations may be designed or intended for oral, rectal, nasal, topical or transmucosal (including buccal, sublingual, ocular, vaginal and rectal) and parenteral (including subcutaneous, intramuscular, intravenous, intradermal, intraperitoneal, intrathecal, intraocular intraparenchymal, intrathecal and epidural) administration. In general, aqueous and non-aqueous liquid or cream formulations are delivered by a parenteral, oral or topical route. In other embodiments, the compositions may be present as an aqueous or a non-aqueous liquid formulation or a solid formulation suitable for administration by any route, e.g., oral, topical, buccal, sublingual, parenteral, aerosol, a depot such as a subcutaneous depot or an intraperitoneal, intraparenchymal or intramuscular depot. In some cases, pharmaceutical compositions are lyophilized. In other cases, pharmaceutical compositions as provided herein contain auxiliary substances such as wetting or emulsifying agents, pH buffering agents, gelling or viscosity enhancing additives, preservatives, flavoring agents, colors, and the like, depending upon the route of administration and the preparation desired. The pharmaceutical compositions may be formulated according to conventional pharmaceutical practice (see, e.g., Remington: *The Science and Practice of Pharmacy,* 20th edition, 2000, ed. A. R. Gennaro, Lippincott Williams & Wilkins, Philadelphia, and *Encyclopedia of Pharmaceutical Technology,* eds. J. Swarbrick and J. C. Boylan, 1988-1999, Marcel Dekker, New York).

The preferred route may vary with, for example, the subject's pathological condition or weight or the subject's response to therapy or that is appropriate to the circumstances. The formulations can also be administered by two or more routes, where the delivery methods are essentially simultaneous or they may be essentially sequential with little or no temporal overlap in the times at which the composition is administered to the subject.

Suitable regimes for initial administration and further doses or for sequential administrations also are variable, may include an initial administration followed by subsequent administrations, but nonetheless, may be ascertained by the skilled artisan from this disclosure, the documents cited herein, and the knowledge in the art.

In some cases, educated macrophages may be optionally administered in combination with one or more additional active agents. Such active agents include anti-inflammatory, anti-cytokine, analgesic, antipyretic, antibiotic, and antiviral agents, as well as growth factors and agonists, antagonists, and modulators of immunoregulatory agents (e.g., TNF-α, IL-2, IL-4, IL-6, IL-10, IL-12, IL-13, IL-18, IFN-α, IFN-γ, BAFF, CXCL13, IP-10, VEGF, EPO, EGF, HRG, Hepatocyte Growth Factor (HGF), Hepcidin, including antibodies reactive against any of the foregoing, and antibodies reactive against any of their receptors). Any suitable combination of such active agents is also contemplated. When administered in combination with one or more active agents, educated macrophages can be administered either simultaneously or sequentially with other active agents. For example, victims of ischemic heart injury may simultaneously receive educated macrophages and a blood thinner such as heparin, a glycoprotein IIb/IIIa inhibitor or a P2Y12 inhibitor for a length of time or according to a dosage regimen sufficient to support recovery and to treat, alleviate, or lessen the severity of the ischemic heart injury. In some embodiments, educated macrophages of the present invention may also be administered to a patient simultaneously receiving a stent, bypass graft, ventricular assist device, or other forms of cell therapy. In some embodiments, the educated macrophages are administered prior to, simultaneously with, or following the administration of a second cell therapy such as to improve or enhance engraftment, survival or function of the administered cells.

In some embodiments, educated macrophages are administered to a subject in need thereof using an infusion, topical application, surgical transplantation, or implantation. In an exemplary embodiment, administration is systemic. In such cases, educated macrophages can be provided to a subject in need thereof in a pharmaceutical composition adapted for intravenous administration to subjects. Typically, compositions for intravenous administration are solutions in sterile isotonic aqueous buffer. The use of such buffers and diluents is well known in the art. Where necessary, the composition may also include a local anesthetic to ameliorate any pain at the site of the injection. Generally, the ingredients are supplied either separately or mixed together in unit dosage form, for example, as a cryopreserved concentrate in a hermetically sealed container such as an ampoule indicating the quantity of active agent. Where the composition is to be administered by infusion, it can be dispensed with an infusion bottle containing sterile pharmaceutical grade water or saline. Where the composition is administered by injection, an ampoule of sterile water for injection or saline can be provided so that the ingredients may be mixed prior to administration. In some cases, compositions comprising human educated macrophages are cryopreserved prior to administration.

Therapeutically effective amounts of educated macrophages are administered to a subject in need thereof. An effective dose or amount is an amount sufficient to effect a beneficial or desired clinical result. With regard to methods of the present invention, the effective dose or amount, which can be administered in one or more administrations, is the amount of human educated macrophages sufficient to elicit a therapeutic effect in a subject to whom the cells are administered. In some cases, an effective dose of educated macrophages is about $1\times10^5$ cells/kilogram to about $10\times10^9$ cells/kilogram of body weight of the recipient (e.g., $1\times10^5$ cells/kilogram, $5\times10^5$ cells/kilogram, $1\times10^6$ cells/kilogram, $5\times10^6$ cells/kilogram, $1\times10^7$ cells/kilogram, $5\times10^7$ cells/kilogram, $1\times10^8$ cells/kilogram, $5\times10^8$ cells/kilogram, or $1\times10^9$ cells/kilogram). Effective amounts will be affected by various factors which modify the action of the cells upon administration and the subject's biological response to the cells, e.g., severity of ischemic heart failure, type of damaged tissue, the patient's age, sex, and diet, the severity of inflammation, time of administration, and other clinical factors.

Therapeutically effective amounts for administration to a human subject can be determined in animal tests and any art-accepted methods for scaling an amount determined to be effective for an animal for human administration. For example, an amount can be initially measured to be effective in an animal model (e.g., to achieve a beneficial or desired clinical result). The amount obtained from the animal model can be used in formulating an effective amount for humans by using conversion factors known in the art. The effective amount obtained in one animal model can also be converted for another animal by using suitable conversion factors such as, for example, body surface area factors.

It is to be understood that, for any particular subject, specific dosage regimes should be adjusted over time according to the individual need and the professional judgment of the person administering or supervising the administration of the educated macrophages. For example, an educated macrophage dosage for a particular subject which ischemic heart failure can be increased if the lower dose does not elicit a detectable or sufficient improvement in heart function. Conversely, the dosage can be decreased if the ischemic heart failure is treated or eliminated.

In some cases, therapeutically effective amounts of educated macrophages can be determined by, for example, measuring the effects of a therapeutic in a subject by incrementally increasing the dosage until the desired symptomatic relief level is achieved. A continuing or repeated dose regimen can also be used to achieve or maintain the desired result. Any other techniques known in the art can be used as well in determining the effective amount range. Of course, the specific effective amount will vary with such factors as the particular disease state being treated, the physical condition of the subject, the type of animal being treated, the duration of the treatment, route of administration, and the nature of any concurrent therapy.

Following administration of educated macrophages to an individual subject afflicted by, prone to, or likely to develop a disease or injury described herein, a clinical symptom or feature associated with the disease or injury is observed and assessed for a positive or negative change. For example, for methods of treating ischemic heart failure in a subject, positive or negative changes in the subject's heart function during or following treatment may be determined by any measure known to those of skill in the art including, without limitation, measuring end systolic pressure, measuring end diastolic pressure, measuring end diastolic volume, measuring end systolic volume, measuring cardiac ejection fraction, measuring cardiac output, measuring contractility (end systolic pressure volume relationship, stroke work or preload recruitable stroke work), and measuring infarct size.

In some embodiments, the disclosed injectable compositions may include one or more fragments of the engineered CF-ECMs and a population of educated macrophages, along with an injectable pharmaceutically-acceptable carrier, where the fragments of the CF-ECM are sufficiently small to be able to freely pass through a hypodermic needle opening. Methods of making the engineered CF-ECM and information regarding its use in injectable compositions are disclosed in, for example, U.S. Pat. No. 8,802,144 and U.S. Patent Publication No. US 2016/0354447, both of which are incorporated herein by reference.

In some embodiments, cardiac specific educated macrophages are administered with an injectable CF-ECM in a treatment in which the CF-ECM is administered prior to macrophage administration to provide an in situ niche for macrophage engraftment, retention and functionality. In some embodiments, the CF-ECM is administered simultaneously in a single composition with the macrophages. In some embodiments, the CF-ECM is infused or implanted with tissue-specific extracellular factors prior to use as a carrier for the educated macrophages.

In some embodiments, the injectable composition may be used to treat cardiac disease or injury, ischemic limb injury, or other injury due to the interruption of blood supply to a tissue. In some cases, the injectable composition is delivered into an endocardial wall of a heart chamber using any appropriate means for trans-endocardial delivery. For example, a delivery catheter can be used to deliver the injectable composition for treatment of a cardiac disease or condition. Other delivery devices can be used to achieve therapeutic or diagnostic delivery of an injectable composition as described herein. For example, the injectable composition can be delivered using a cardiac needle tip injection catheter such as the Myostar (Biosense Webster), Helix (Biocardia), Bullfrog (Mercator MedSystems) or C-Cath (Cardio3Biosciences). Advantageously, delivery of an injectable composition by the injection methods described herein is minimally invasive and can be achieved without general anesthesia, extracorporeal circulation (e.g., circulation via a heart-lung machine), circulatory support, or a chest opening. Accordingly, complication prospects and risks to the patient are substantially lower.

In some cases, the injectable composition is delivered to the outer heart wall (epicardium) using any appropriate means for epicardial delivery. For example, epicardial delivery of an injectable composition described herein can be achieved using a delivery device comprising a needle and/or syringe. In one embodiment, a suitable delivery vehicle may be cardiac fibroblast derived extracellular matrix. In one embodiment, a suitable delivery vehicle may be cardiac fibroblast derived extracellular matrix embedded with cardiac fibroblast exosomes.

In any of the methods of the present invention, the donor and the recipient of the educated macrophages can be a single individual or different individuals, for example, allogeneic or xenogeneic individuals. As used herein, the term "allogeneic" refers to something that is genetically different although belonging to or obtained from the same species (e.g., allogeneic tissue grafts or organ transplants). "Xenogeneic" means the cells could be derived from a different species.

The present invention has been described in terms of one or more preferred embodiments, and it should be appreciated that many equivalents, alternatives, variations, and modifications, aside from those expressly stated, are possible and within the scope of the invention.

The invention will be more fully understood upon consideration of the following non-limiting Examples.

Example 1

The embodiment described here demonstrates the concept that cardiac-specific anti-inflammatory tissue-reparative macrophages can be bioengineered by conditioning circulating monocytes with cardiac fibroblast-derived exosomes and cardiac fibroblast derived extracellular matrix. We describe these macrophages as Cardiac Fibroblast Exosome-Educated Macrophages (CF-EEM). In preliminary studies described herein, we observed that CF-EEM has a unique cell surface immunophenotype that is different than any other known macrophage population. In a proof of concept in vivo study, CF-EEM were injected into an immunocompetent rat myocardial infarction model. We observed a significant reduction in infarct size, a significant improvement in heart function and no evidence of immune rejection in the CF-EEM treated rats compared to historical control animals.

We discovered that bone marrow mesenchymal stem cells (BM-MSC) (Hematti et al.), cardiac fibroblasts (CF) and cardiac fibroblast-derived extracellular matrix (CF-ECM) can educate monocytes to become unique educated macrophages. Our results suggest significant monocyte-to-macrophage conversion using exosomes isolated from human CFs and using human CF derived extra-cellular matrix. These cardiac-specific anti-inflammatory tissue-reparative subpopulations offer a novel immunotherapeutic approach to repair the injured cardiac microenvironment.

In the example described herein, human CF-EEMs are generated by co-culturing macrophages with cardiac fibroblast-derived exosomes and subsequently administered into immunocompromised rats that have undergone coronary artery ligation to induce a large MI. Ejection fraction, infarct size, pressure-volume hemodynamics, angiogenic responses, fibro-healing responses, and CF-EEM retention are measured.

Methods

Isolation and cultivation of MSCs, macrophages and cardio-fibroblasts (CF)—We used human blood and bone marrow to derive monocytes and MSCs, respectively. All protocols were approved by the Health Sciences Institutional Review Board of University of Wisconsin-Madison School of Medicine and Public Health. Monocytes were isolated from human peripheral blood by using magnetic bead separation methods according to manufacturers' protocols. Briefly, peripheral blood mononuclear cells were collected from the blood of healthy donors by density gradient separation using Percoll™ (GE Healthcare Bio-Sciences, Piscataway, N.J., USA). Red blood cells were lysed by incubating cells in ACK lysis buffer (Lonza, Walkersville, Md.) for 3 minutes and mononuclear cells were washed with phosphate-buffered saline (PBS). To reduce platelet contamination, cell suspensions were centrifuged at 300-700 rpm for 10 minutes and cell pellets were re-suspended in autoMACS™ running buffer (Miltenyi Biotec, cat #130-091-221). To isolate monocytes, the cells were incubated with anti-human CD14 microbeads (Miltenyi Biotech, Auburn, Calif., USA) for 15 minutes at 4° C. After washing to remove unbound antibody, cell separation was done using autoMACS™ Pro Separator (Miltenyi Biotech). Purity of isolated CD14$^+$ cells was >95% when checked with flow cytometry. Purified CD14$^+$ monocytes were plated either into six-well cell culture plates for flow cytometry or in 75-cm$^2$ filter cap cell culture flask (Greiner Bio-One, Monroe, N.C., USA) for exosome isolation or in vitro assays at a concentration of 0.5-1×10⁶ per well or flask in Iscove's modified Dulbecco's medium (IMDM) without phenol (Gibco Life Technologies/ThermoFisher Scientific, Grand Island, N.Y.) supplemented with 10% human serum blood type AB (Mediatech, Herndon, Va., USA), 1× nonessential amino acids (Lonza, Walkersville, Md., USA), 1 mM sodium pyruvate (Mediatech), and 4 µg/mL recombinant human insulin (Invitrogen). Cells were cultured for 7 days to differentiate to macrophages at 37° C. with 5% $CO_2$.

Mesenchymal stem cells (MSCs) were isolated from bone marrow filters left over after bone marrow harvest from normal healthy donors. Briefly, leftover bone marrow cells trapped in filter were washed with PBS and mononuclear cells were separated using Ficoll-Hypaque 1.073 (GE Healthcare Bio-Sciences, USA) according to manufacturer's protocol. Red blood cells were lysed with 3-minute incubation in ACK lysis buffer and mononuclear cells were suspended in α-Minimum Essential Medium (Corning CellGro, Manassas, Va.) supplemented with 10% fetal bovine serum (FBS) (US origin, uncharacterized; Hyclone, Logan, Utah, USA), 1× nonessential amino acids, and 4 mM L-glutamine (Invitrogen, Carlsbad, Calif., USA). Cells were cultured in 75-cm² filter cap cell culture flasks. Cells (passage 0) were harvested by removing medium, washing with phosphate-buffered saline (PBS) then using TrypLE™ cell dissociation enzyme (Invitrogen) to detach the adherent cells and then re-plated into new flasks.

Tissue collection protocols have been reviewed and approved by the UW School of Medicine and Public Health institutional review board (IRB). Cadaveric cardiac tissue was harvested from recently deceased brain-dead donors at the University of Wisconsin-Madison Hospital & Clinics (UWHC) in Madison, Wis. under aseptic surgical conditions by the UW Organ Procurement Organization (OPO) and delivered to the investigators for cardiac fibroblast isolation.

Cardiac fibroblasts were isolated from a modified protocol previously described. Briefly, hearts were obtained by the UWHC OPO using aseptic technique. Upon receipt, the fresh organ was removed from the transport container and the sterile packaging opened in a biological safety cabinet. 20-200 grams of left ventricle was dissected out. The dissected tissue was then coarsely chopped and 5-6 grams processed in gentleMACS™ C tubes (MACS Miltenyi Biotech/130-093-235). The tissue was then run through a standard cardiac dispersion protocol on the Miltenyi gentleMACS™ Dissociator. 1.25 g Liberase™ (Roche Diagnostics/05401119001) was then added to each C tube and incubated at 37° C. with constant agitation for up to 120 minutes to form a single cell suspension. The cell suspension was then sieved through a 200 µm Pluristrainer (PluriBead/43-50200-03). The resulting cell suspension was centrifuged at 1000×g for 30 minutes. The cell suspension was then suspended in complete Lonza FGF-3 medium (Lonza-CC-4526) and plated on to T75 tissue culture treated flasks (Falcon) for 120 minutes. The plates were then aspirated and fresh Lonza FGF-3 medium added to the flask. The cardiac fibroblasts were cultured under standard conditions (5% $CO_2$, 37° C., 100% Humidity) and the medium was changed every 2-3 days until the cardiac fibroblasts reached 50%-90% confluency when they were passaged using TrypLE™ E select.

Isolation of extracellular vesicles (EVs) containing exosomes and micro-vesicles—Cells grown to confluence in 75-cm² filter cap cell culture flasks were then washed once with PBS, and the medium was replaced with STEMPRO™ MSC serum-free medium (SFM) CTS (A103332-01, Gibco Life Technologies). Cell were incubated for 18-24 hours and the conditioned culture medium was harvested and centrifuged using a Beckman Coulter Allegra® X-15R centrifuge at 2000×g at 4° C. for 20 minutes to remove any detached cells, apoptotic bodies and cell debris. Clarified supernatant culture medium was then centrifuged in a Beckman Coulter Optima™ L-80XP Ultracentrifuge at 100,000 g average at 4° C. for 2 hours with a SW 28 rotor to pellet exosomes. The supernatant was carefully removed, and EV-containing pellets were re-suspended PBS and pooled. Typically we re-suspended the EV pellet at 100 µl PBS/10 ml of CM.

Figure 16:
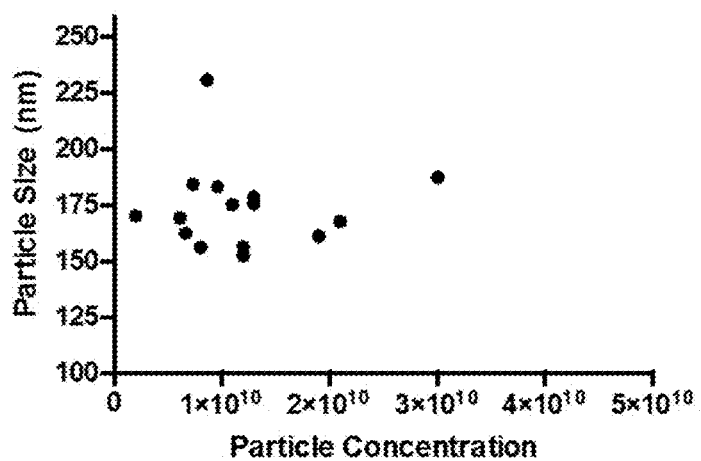
FIG. 16 shows characterization of cardiac fibroblast extracellular vesicles. Cardiac fibroblast exosomes were characterized using a Thermo NanoDrop spectrophotometer for protein determination and approximate RNA concentration by direct absorbance; exosomes were not lysed, stained, or RNA extracted prior to measurements. Particle diameter and concentration were assessed by tunable resistive pulse sensing (TRPS; (qNano, Izon Science Ltd) using a NP150 nanopore membrane at a 47 mm stretch. The concentration of particles was standardized using multi-pressure calibration with 110 nm carboxylated polystyrene beads at a concentration of $1.1 \times 10^{13}$ particles/mL.

Cardiac fibroblast exosome characterization—Cardiac fibroblast exosomes were characterized using a Thermo NanoDrop spectrophotometer for protein determination and approximate RNA concentration by direct absorbance; exosomes were not lysed, stained, or RNA extracted prior to measurements. Particle diameter and concentration were assessed by tunable resistive pulse sensing (TRPS; (qNano, Izon Science Ltd) using a NP150 nanopore membrane at a 47 mm stretch. The concentration of particles was standardized using multi-pressure calibration with 110 nm carboxylated polystyrene beads at a concentration of $1.1 \times 10^{13}$ particles/mL. The results of the CF exosome characterization are shown in FIG. 16.

Exosome total RNA isolation—Exosomes from the cardiac fibroblasts were processed for total RNA isolation using the SeraMir Exosome RNA Purification Column kit (Cat #RA808A-1, System Biosciences, Palo Alto, Calif.) according to the manufacturer's instructions. For each sample, 1 µl of the final RNA eluate was used for measurement of small RNA concentration by Agilent Bioanalyzer Small RNA Assay using Bioanalyzer 2100 Expert instrument (Agilent Technologies, Santa Clara, Calif.).

NGS Library generation and sequencing—From the exosome RNA isolations, small RNA libraries were constructed with the CleanTag Small RNA Library Preparation Kit (TriLink, Cat #L-3206) according to the manufacturer's protocol. The final purified library was quantified with High Sensitivity DNA Reagents (Agilent Technologies, PO #G2933-85004) and High Sensitivity DNA Chips (Agilent Technologies, PO #5067-4626). The libraries were pooled, and the 140 bp to 300 bp region was size selected on an 8% TBE gel (Invitrogen by Life Technologies, Ref #EC6215). The size-selected library is quantified with High Sensitivity DNA 1000 Screen Tape (Agilent Technologies, PO #5067-5584), High Sensitivity D1000 reagents (Agilent Technologies, PO #5067-5585), and the TailorMix HT1 qPCR assay (SeqMatic, Cat #TM-505), followed by a NextSeq High Output single-end sequencing run at SR75 using NextSeq 500/550 High Output v2 kit (Cat #FC-404-2005, Illumina, San Diego, Calif.) according to the manufacturer's instructions. For data analysis on the total RNA isolation and NGS libraries, per gene expected counts in each sample were estimated using RSEM. These counts were filtered, keeping only those genes that had at least one expected count (per gene) in all three samples. Next, the TMM (trimmed method of means) was computed to normalize the counts. Finally, the counts per million (CPM) were computed and the coefficient of variation (CV=stdev/mean) calculated for each gene cross the three samples. The results of the RNA-Seq from the CF exosome total RNA isolation are shown in FIG. 17.

Education of macrophages with MSCs (MEM) or using EVs from MSCs, CF or macrophages (EEMs)—For education of macrophages by co-culture with MSCs to produce MSC-educated macrophages (MEMs), macrophages on day 7 were supplemented with fresh macrophage medium containing MSCs at a ratio of 10:1 macrophages to MSCs and cultivated for 3 days. For education using EVs, EVs from MSCs, CFs, or macrophages were added to macrophages on day 7 and cultivated for 3 days. Typically, cells were educated in either 6 well plates (2 ml) or 75-cm$^2$ filter cap cell culture flasks (10 ml) using either 60 µl or 300 µl of EVs respectively. Cell were harvested by removing the medium, washing with phosphate-buffered saline (PBS) then using TrypLE™ cell dissociation enzyme (Invitrogen) and/or a cell scraper.

Flow cytometry—Macrophages, MEMs or EV educated macrophages (EEMs) at day +10 of culture were collected, counted and incubated with Fc block (BD Pharmingen, cat #: 564220) and stained at 4° C. for 20 minutes in antibody diluent (PBS with 2% FBS) with anti-human antibodies including PE-Cy7-CD90 (5E10, cat #328124), FITC-CD163 (GHI/61, cat #333618), FITC-CD39 (A1, cat #328206), PE-CD206 (15-2, cat #321106), PerCP/Cy5.5-CD14 (HCD14, cat #325622, APC-PD-L1 (29E.2A3, cat #329708), APC-PD-L2 (24F.10C12, cat #329608), Pacific Blue-HLA-DR/MHC II (L234, cat #307633), BV421-CD16 (3G8, cat #302038), and BV510-CD86 (IT2.2, cat #305432). All antibodies were purchased from BioLegend (San Diego, Calif.) except BV510-CD73 (AD2, cat #563198) from BD Pharmingen (San Jose, Calif.). Compensation was performed using Ultracomp e-beads (Cat #01-2222-42) ebiosciences, (San Diego, Calif.). Gating of MSCs and macrophages was achieved using CD90 antibodies, specific for MSC and CD14 antibodies, specific for macrophages. Flow cytometry data were acquired on an Accuri C6 cytometer (BD Biosciences, San Jose Calif.) or MACSQuant analyzer 10 (Miltenyi Biotec Inc, San Diego Calif.). MACSQuant files were converted to .fcs files using The MACSQuantify™ Software. The data were analyzed using FlowJo™ software (TreeStar).

Gene expression analysis—RNA was isolated from cells using RNeasy micro kit (Qiagen, Valencia, Calif., USA), and the quality of isolated RNA was checked using Nanodrop 1000 (Fisher Scientific, Pittsburgh, Pa., USA). RNA was converted to cDNA using Quantitect reverse transcription kit (Qiagen). Quantitative polymerase chain reaction (qPCR) was performed using Power SYBR green master mix (Applied Biosystems, Foster City, Calif., USA) on StepOne Plus instrument (Applied Biosystems) using standard protocols. Verified primers were purchased from Qiagen. The threshold cycle (Ct) value for each gene was normalized by the average Ct number of a common housekeeping gene (GAPDH).

Activated T-cell suppression assay—The activated T-cell suppression assay was performed in 48 well tissue culture plates. Frozen stocks of peripheral blood mononuclear cells (PBMCs) containing T cells and MSCs, macrophages and BM-EEMs were freshly cultivated in medium (IPA medium) consisting of RPMI-1640 containing 10% heat inactivated FBS, 1× non-essential amino acids (NEAA) (Mediatech, Inc., Manassas, Va.), 1× Glutamine (Mediatech, Inc.), 1× Na Pyruvate (Sigma-Aldrich), and 1× HEPES buffer (Sigma-Aldrich, St. Louis, Mo.). To measure proliferation, PBMCs were first labeled with carboxyfluorescein succinate-ester (CFSE) at a final concentration of 1 uM for 10 minutes, at 37° C. in the dark, mixing at the 5 minute time point to ensure homogeneous labeling. An equal volume of cold FBS was added for 1 minute to stop the CFSE labeling reaction. PBMCs were then washed twice with IPA medium before reconstitution at 4×10$^6$/ml. One hundred microliters (4×10$^5$) of CF SE-labeled PBMCs was added to each well containing MSCs, macrophages and BM-EEMs. Ratios of antibody-activated PBMCs to MSC, macrophages and BM-EEMs evaluated in this assay include 1:0 (positive control-no suppression), 1:1, 1:0.5, 1:0.2, 1:0.1, and 1:0.05. MSCs were included in this assay to serve as a positive control cell group because MSCs are known to strongly inhibit PBMC proliferation. For a 1:1 (PBMC:MSC) ratio, 4×10$^5$ MSCs (100 µl) were plated and then titrated further to 2×10$^4$ to achieve a 1:0.05 (PBMC:MSC) ratio. To establish a reliable gating strategy, non-activated control was used consisting of a 1:0.05 PBMC:MSC cell ratio without the addition of activation antibodies (anti-CD3 and anti-CD28) (negative control-no T-cell activation). The various ratios of cells from each group (PBMC:MSC), (PBMC:macrophages) and (PBMC:BM-EEMs) were added to wells in the plate and the cells were then allowed to settle at 37° C. The PBMCs in the cell mixture were then activated with anti-CD3 and anti-CD28 antibodies (clones UCHT1 and 37407, respectively) (R&D Systems, Inc., Minneapolis, Minn.). Specifically a 100 µl mixture of 4× concentrated anti-huCD3 and anti-huCD28 antibodies (10 ug/mL and 2 ug/mL, respectively) was added to each well except for the 1:0.05 (PBMC:MSC) non-activated control which received 100 µl of IPA medium for a total volume of 400 µl per well. The cell mixture was cultured for 4 days at 37° C. with 5% CO2. The PBMCs were recovered from each well by pipetting up and down to mix and added to a 5 ml flow tube. CD4+ T helper cells and CD8+ cytotoxic cells were each analyzed for proliferation using standard flow cytometry methodology. Anti-human APC –CD4 or CD8– (R&D Systems, Inc.) was used to gate the T-cell types. All proliferation analyses were performed using an Accuri C6 flow cytometer (BD Biosciences, Inc., San Jose, Calif.) and the associated C6 Plus software was used for the CFSE analysis.

We also tested whether either macrophages or BM-EEMs mixed at highest ratio with the PBMCs (1:1 ratio) could themselves promote proliferation of the PBMCs without requiring antibody activation with anti-huCD3 and anti-huCD28 antibodies. As with the non-activation group above, 100 µl of medium without the activating antibodies were added to the mixture of cells. As above the cell mixture was cultured for 4 days at 37° C., harvested and both the CD4+ T helper cells and CD8+ cytotoxic cells were analyzed for proliferation using standard flow cytometry methodology. Anti-human APC –CD4 or CD8– (R&D Systems, Inc.) was used to gate the T-cell types.

Ischemic heart failure animal model—A pilot of n=10 rats underwent treatment with human CF-EEM injected into the infarct border zone 2 days post MI. After 28 days, there was a significant improvement in contractility, fractional shortening and a reduction in infarct size compared to baseline (FIGS. 12A-12E), and compared to historical controls in our past experience with this model.

Immunocompetent Lewis rats were purchased from Harlan Laboratories. Following induction of isoflurane anesthesia (3%), the rat was intubated and placed on a rat ventilator and maintained on 2% isoflurane. A left lateral incision through the fourth intercostal space was made to expose the heart. After visualizing the left anterior descending coronary artery, a 7-0 or 8-0 Prolene suture was placed through the myocardium in the anterolateral wall and secured. Coronary artery entrapment was confirmed by observing blanching of the distal circulation at the ventricular apex. Absorbable sutures were used to close the ribs and muscle layers. The overlying skin was closed by additional 6-0 nylon or silk sutures, after which rats were recovered.

Two days post myocardial infarction surviving rats were anesthetized, intubated and the heart exposed as described above. 1×10$^6$ human CF-EEM were injected into the border zone of the infarct and the incision closed as described above. Animals were followed and then sacrificed 28 days post treatment.

Rats underwent transthoracic echocardiography at baseline day 0 (treatment day), and day 28. Measurements include: infarct size, fractional shortening, end systolic volume, end diastolic volume and wall thickness. Prior to sacrifice, invasive pressure volume loop assessment was carried out, end systolic pressure, end diastolic pressure, end systolic volume, end diastolic volume, preload independent contractility and pressure-volume relationships were measured using a conductance catheter with inferior vena cava clamp. Measurements were performed by the UW Animal Physiology Core lab who were blinded to treatment assignment.

At time of sacrifice, hearts were excised and sectioned. LV mass and infarct size were measured. Sections were stained and quantitatively graded for vascular density, tissue necrosis, and myocardial fibrosis by a blinded board-certified UW RARC veterinary pathologist.

Results

Figure 2A:
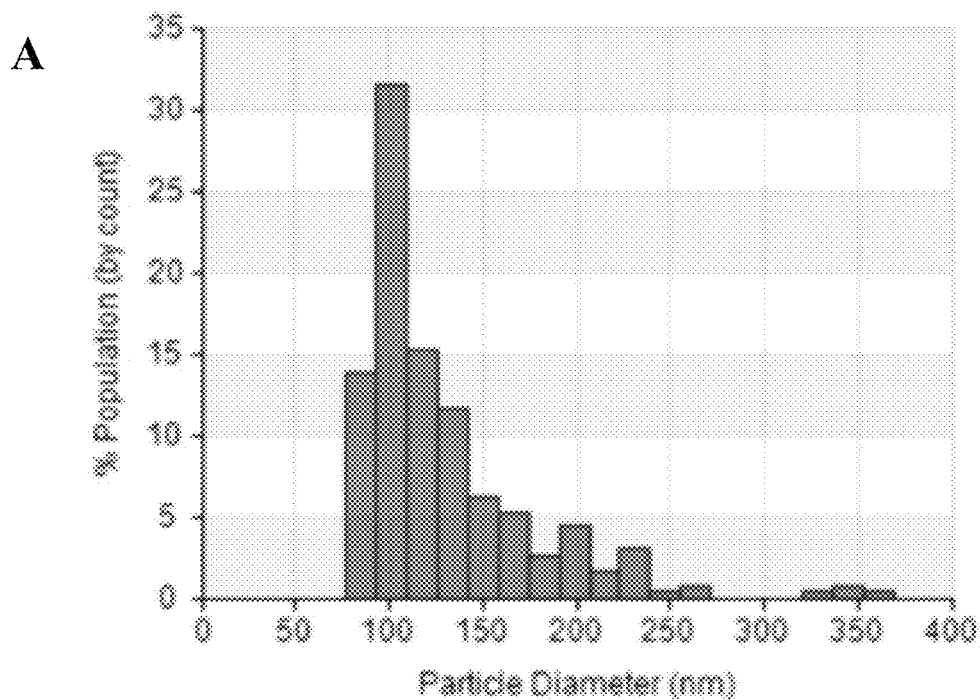
FIGS. 2A-2B show exosome size distribution characterization using an IZON nanoparticle system. (A) shows characterization of mesenchymal stem cell exosomes, with a protein concentration of 2.2 mg/ml, an RNA concentration of 61.8 ng/ml, a mean particle diameter of 123 nm, a mode particle diameter of 93 nm, and a concentration of $6.0 \times 10^{11}$ particles/ml. (B) shows characterization of cardiac fibroblast exosomes, with a volume of 25 μL, a protein concentration of 0.17 mg/ml, an RNA concentration of 13.6 ng/μl, an A260/280 of 1.45, a mean particle diameter of 165.9 nm, and a concentration of $3.2 \times 10^{11}$ particles/ml.
Figure 2B:
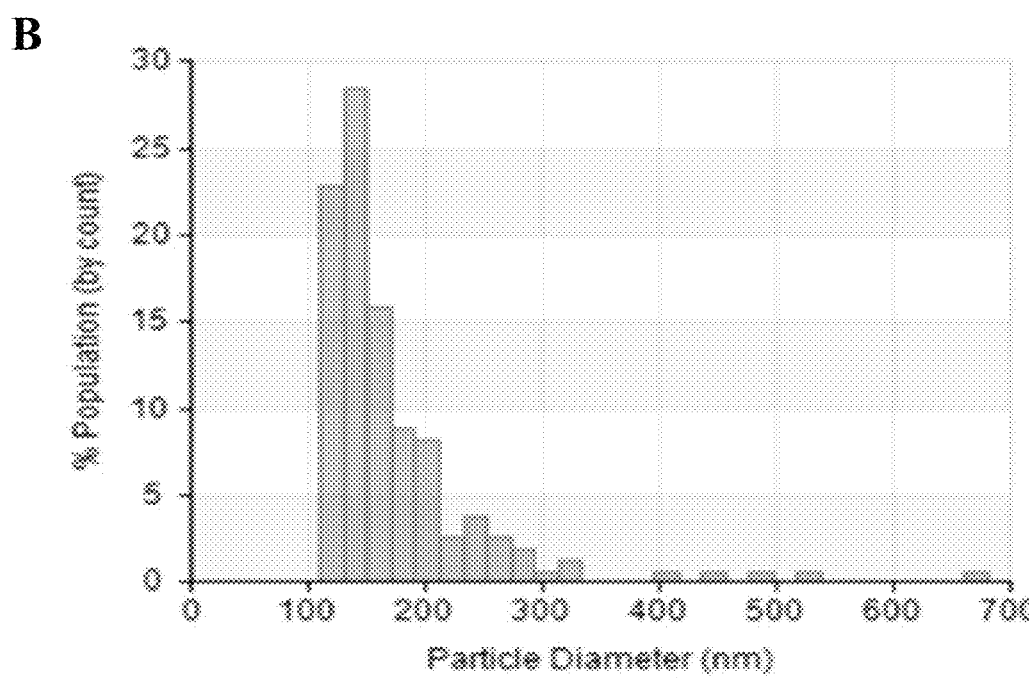
Figure 3A:
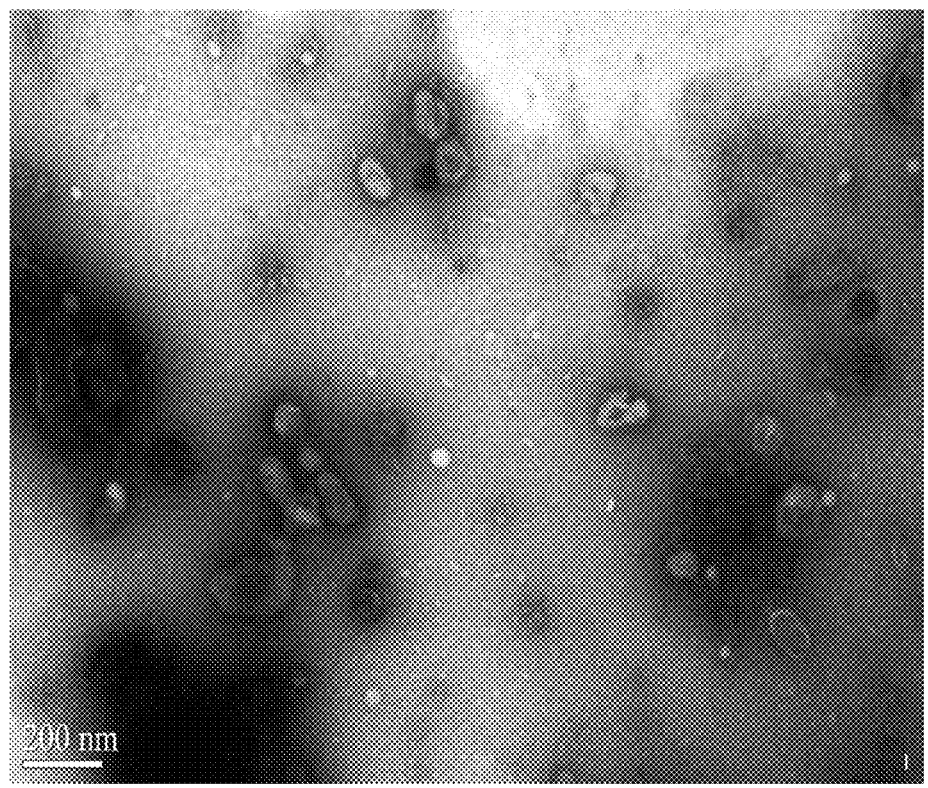
FIGS. 3A-3B show transmission electron microscopy images of (A) mesenchymal stem cell (MSC) exosomes and (B) cardiac fibroblast (CF) exosomes. Several microliters of each prep were spotted onto Formvar EM grids, allowed to dry, washed with PBS and then stained with uranyl acetate. Based on size, most of the EVs released by the MSCs or CFs are within the size range of exosomes.
Figure 3B:
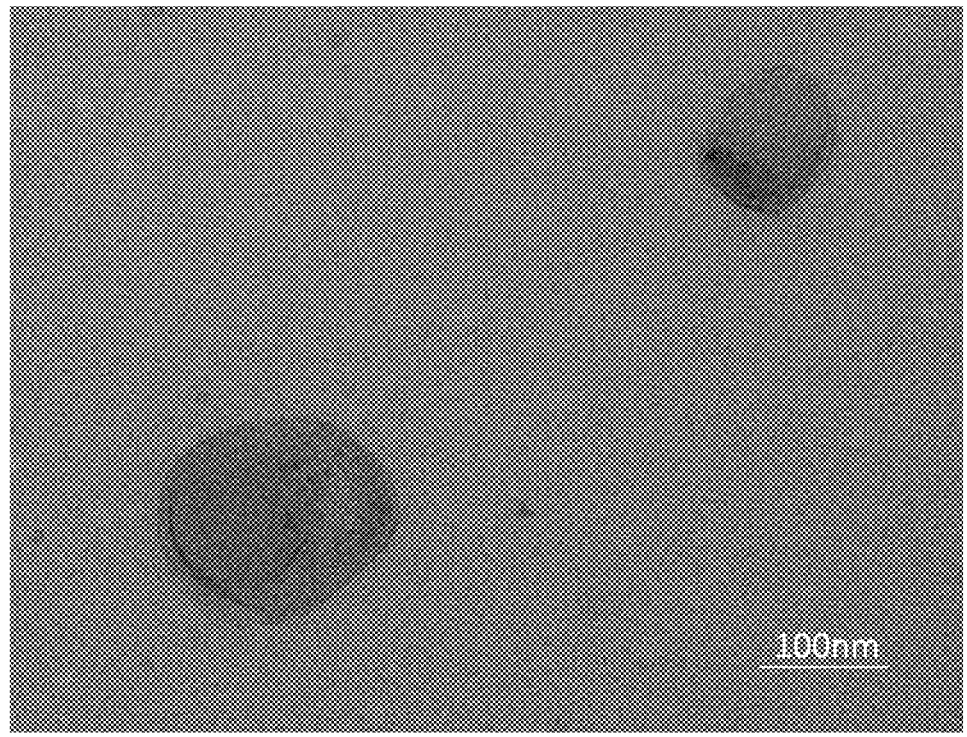
Figure 4A:
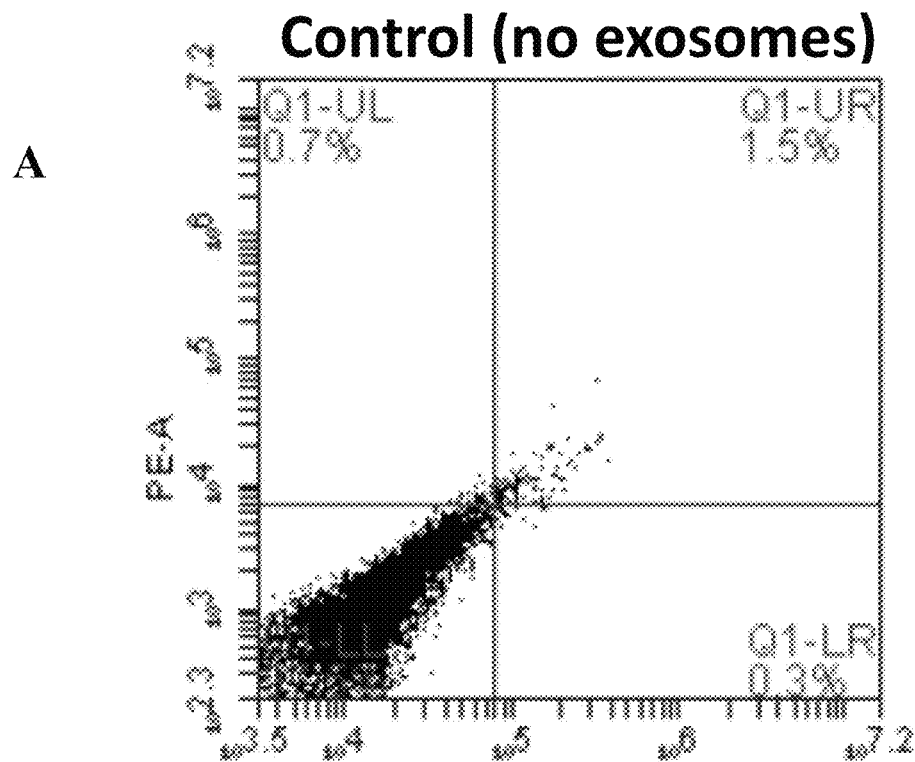
FIGS. 4A-4B depict testing of exosome functionality by lipophilic dye transfer by mesenchymal stem cell exosomes into endothelial cells.
Figure 4B:
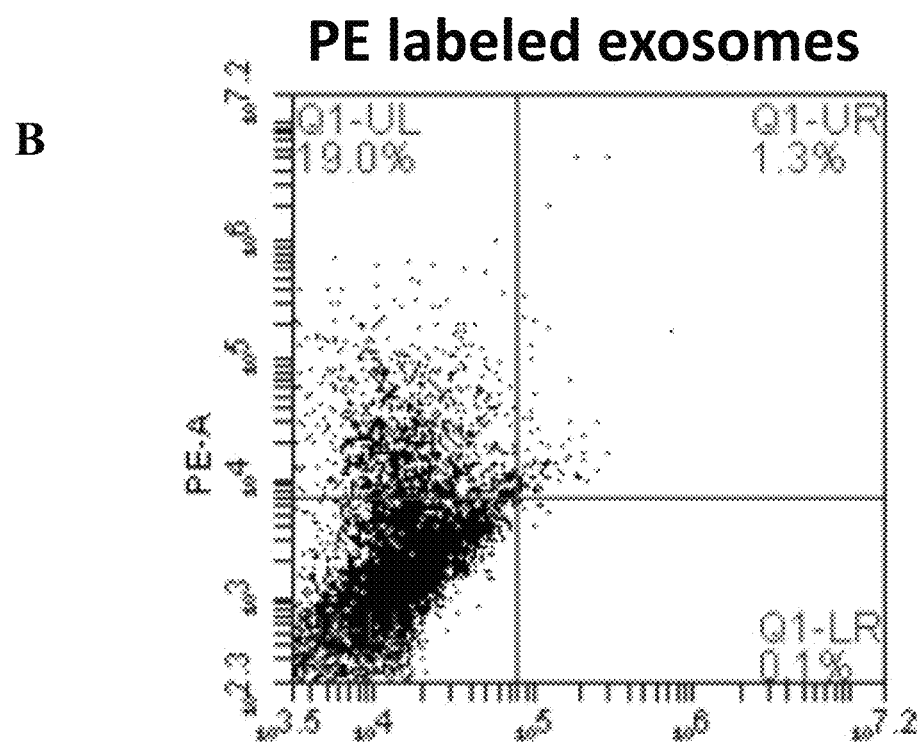
Figures 5A, 5B, 5C, 5D, 5E, 5F, 5G, 5H, 5I, 5J:
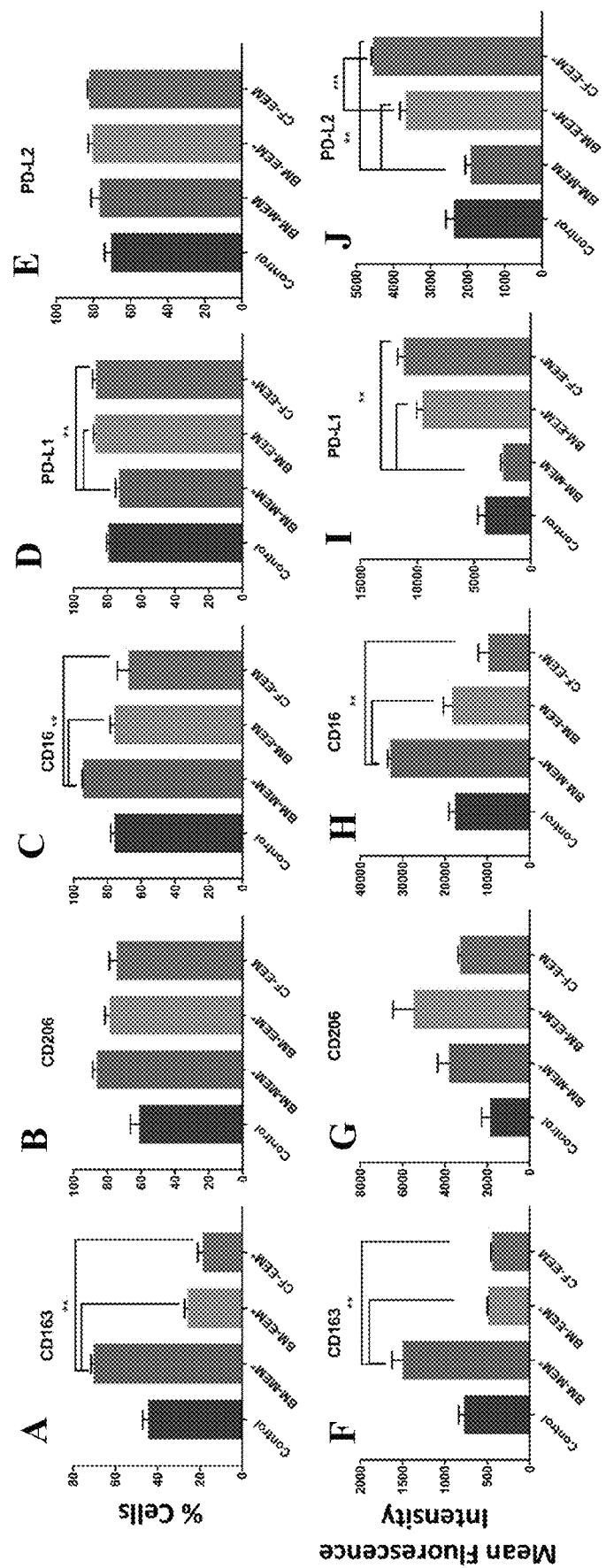
FIGS. 5A-5J show the surface marker profile of macrophages educated with exosomes derived from bone marrow and cardiac fibroblasts. Levels of expression profile markers were measured by flow cytometry comparing macrophages (control) with educated macrophages generated by co-cultivation of monocytes with BM-MSCs (BM-MEM), exosomes derived from bone marrow (BM-EEM), or exosomes derived from cardiac fibroblasts (CF-EEM).
Figures 6A, 6B, 6C, 6D:
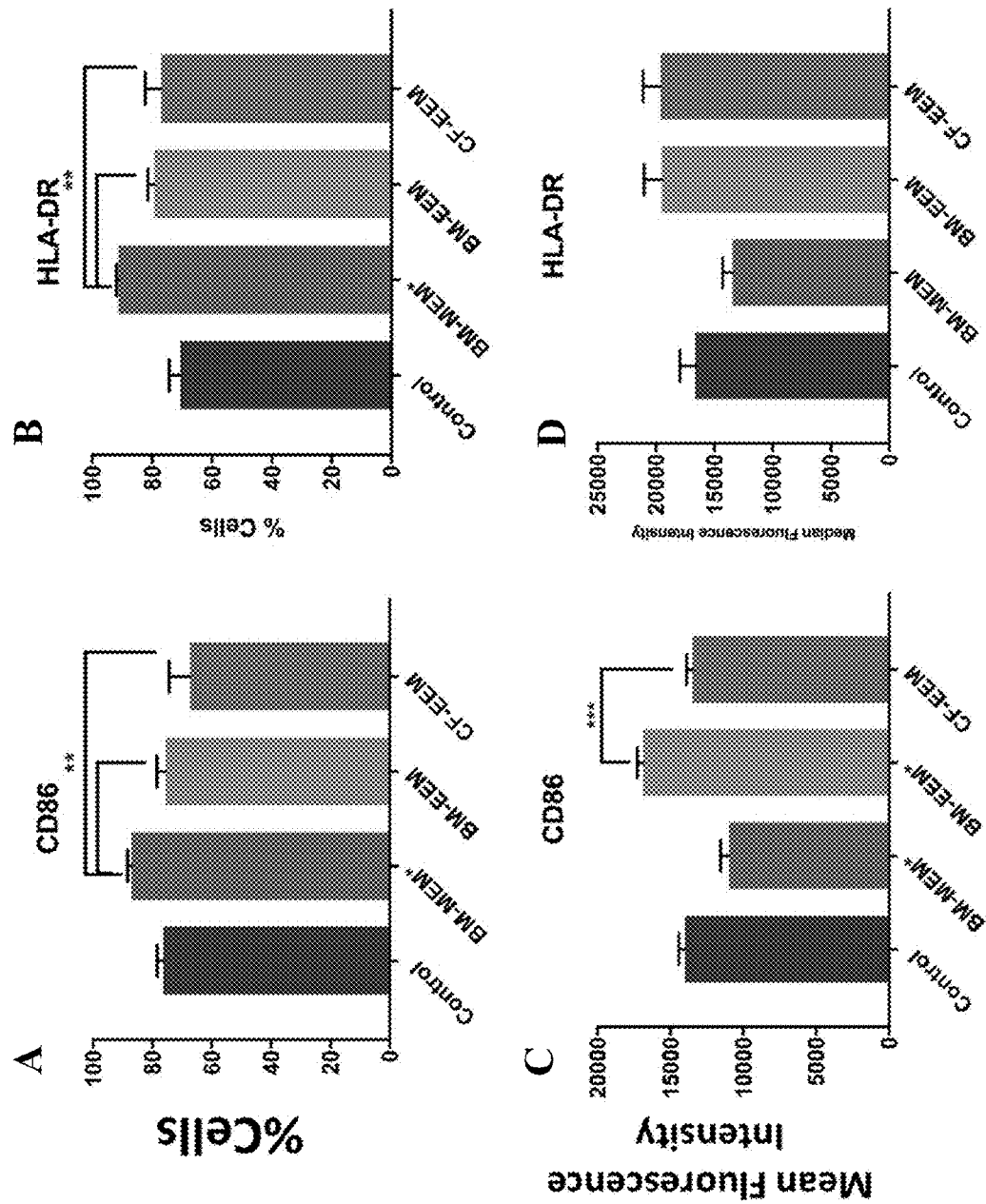
FIGS. 6A-6D show the M1 surface marker profile of macrophages educated with exosomes derived from bone marrow (BM-EEM), or exosomes derived from cardiac fibroblasts (CF-EEM). Levels of M1 expression profile markers were measured by flow cytometry comparing macrophages (control) with macrophages educated by co-cultivation of monocytes with BM-MSCs (BM-MEM) or with exosomes derived from bone marrow (BM-EEM), or with exosomes derived from cardiac fibroblasts (CF-EEM). CD86 mean fluorescence intensity (MFI) is statistically lower in CF-EEM compared to BM-EEM. CD86 is the co-stimulatory signal for T-cell activation and HLA-DR is the ligand for T-cell receptor.
Figures 7A, 7B, 7C, 7D, 7E:
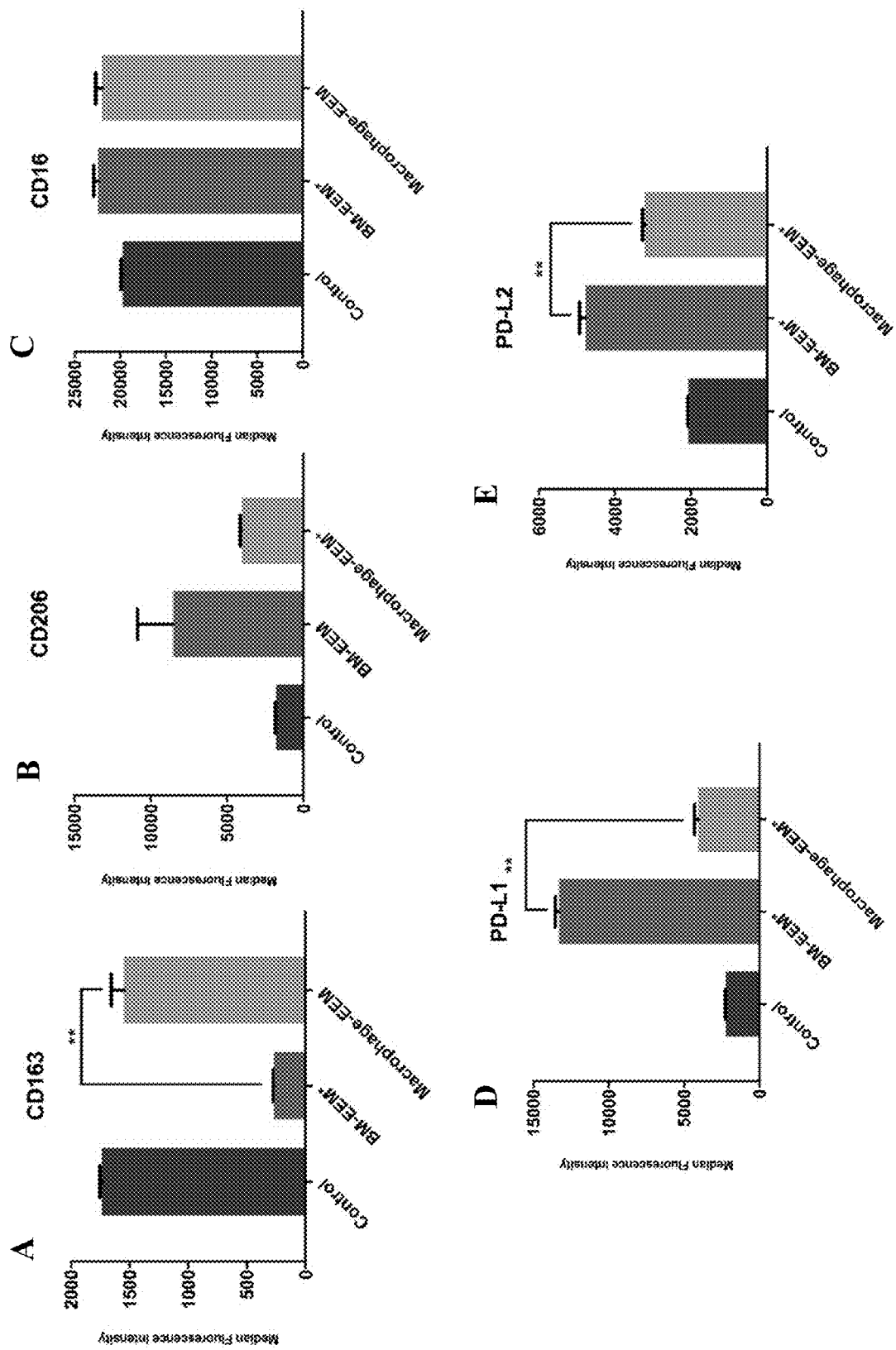
FIGS. 7A-7E compare the canonical M2 surface marker expression in macrophages educated by co-culture with exosomes from BM-MSCs (BM-EEM) or exosomes derived from macrophages (macrophage-EEM). Exosomes from macrophage cultures do not induce an M2 phenotype in macrophages.

Exosomes were isolated from human bone marrow mesenchymal stem cells and human cardiac fibroblasts and characterized for particle size (diameter), protein and RNA concentration and exosome concentrations (FIGS. 2A-2B, Table 2). We found that exosomes derived from MSCs and cardiac fibroblasts were different in diameter and protein/RNA concentration. In general, cardiac fibroblast-derived exosomes were larger than MSC-derived exosomes, but had less protein and RNA. Sample transmission electron microscopy images of exosomes derived from mesenchymal stem cells (FIG. 3A) and cardiac fibroblasts (FIG. 3B) were taken. Additionally, functionality testing of the MSC-derived exosomes (FIGS. 4A-4B) shows the exosomes are functional and capable of lipophilic dye transfer into endothelial cells.

Figure 15:
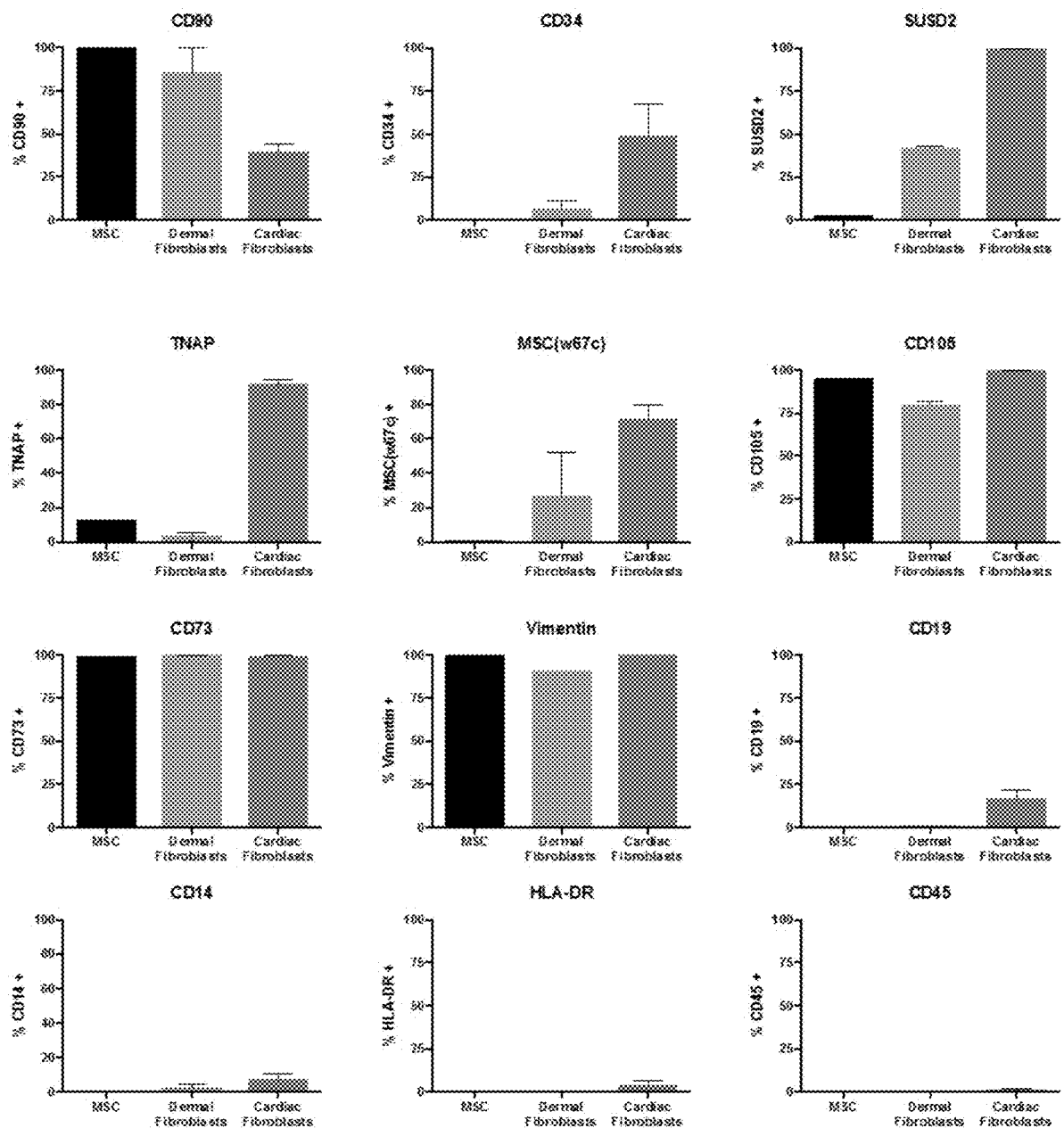
FIG. 15 shows cardiac fibroblast characterization. Cardiac fibroblasts have a unique surface marker and internal marker phenotype. Human cardiac fibroblasts differentially express CD90, CD34, SUSD2, w67c, and TNAP by flow cytometry analysis compared to MSCs and dermal fibroblasts. In addition, cardiac fibroblasts also express GATA 4, which is not expressed in MSCs or dermal fibroblasts.
Figure 15:
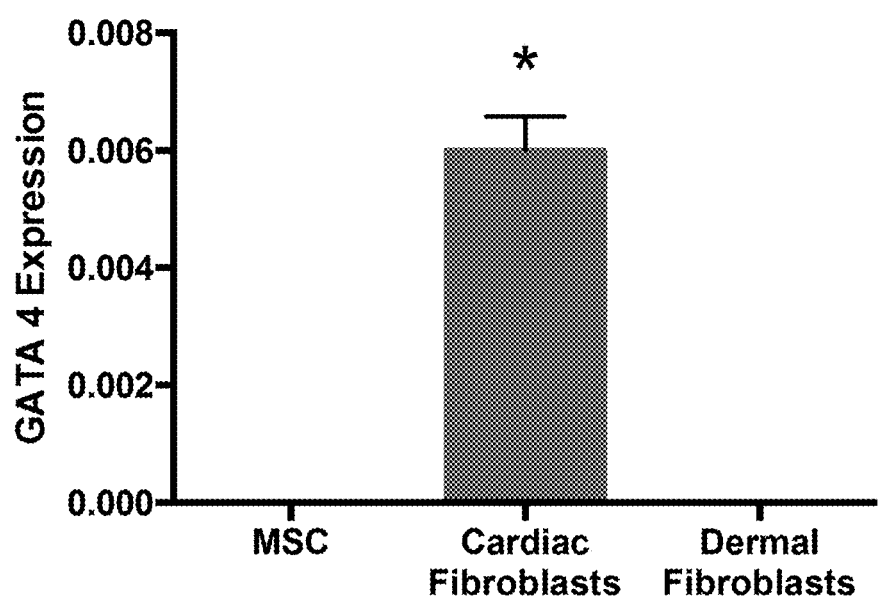

As depicted in FIG. 15, human cardiac fibroblasts differentially express CD90, CD34, SUSD2, w67C, and TNAP compared to either BM-MSCs or dermal fibroblasts. In addition, cardiac fibroblasts also express GATA 4, which is not expressed in MSCs or dermal fibroblasts.

Following co-culture of macrophages with bone marrow-MSC exosomes or cardiac fibroblast exosomes, expression profiles and phenotypes of the educated macrophages were analyzed as depicted in FIGS. 5A-5J. Canonical M2 macrophage surface markers were examined by flow cytometry. Significant difference was found in both surface marker percentages and fluorescence intensity of the markers. Specifically, exosome education results in significant difference among bone marrow MSC (BM-MEM), BM-EEM and CF-EEM groups. Importantly, bone marrow exosome- and cardiac fibroblast exosome-educated macrophages display different phenotypes. In a control experiment, exosomes isolated from macrophage cultures were used in co-culture with CD14$^+$ cells but were unable to induce an anti-inflammatory phenotype in the educated macrophages, and displayed the same surface marker phenotype as the untreated control macrophages, thus showing that the anti-inflammatory phenotype education is unique to tissue-specific (i.e., MSC or CF) exosomes (FIGS. 7A-7E)

Also, M1 (inflammatory) macrophage surface markers in the educated macrophages were examined by flow cytometry, as depicted in FIGS. 6A-6D. Significant difference was found in both surface marker percentages and fluorescence intensity of the markers. Specifically, exosome education results in significant difference among bone marrow MSC (BM-MEM), BM-EEM and CF-EEM groups. Bone marrow and cardiac fibroblast exosome educated anti-inflammatory macrophages have reduced M1 markers compared to macrophages generated by co-cultivation with bone marrow MSCs.

TABLE 2

Characterization by IZON qNano System of exosomes generated from multiple sources

| Cell type | lot | Culture round | Mean particle size (nm) | Mode particle size (nm) | Particle concentration/ ml | Approx Particle concentration/ $10^6$ cells |
|---|---|---|---|---|---|---|
| BM MSC | 15PH05 P3 | first | 123 | 93 | $6.0 \times 10^{11}$ | $6.6 \times 10^{10}$ |
| BM MSC | 15PH05 P3 | first (repeat)* | 92 | 64 | $7.6 \times 10^{10}$ | $8.4 \times 10^9$ |
| BM MSC | 15PH07 P4 | first | 85 | 84 | $1.8 \times 10^{11}$ | $2.0 \times 10^{10}$ |
| BM MSC | 15PH09 P3 | first | 86 | 61 | $2.0 \times 10^{11}$ | $2.2 \times 10^{10}$ |
| BM MSC | 15PH05 P4 | first | 169 | 114 | $1.3 \times 10^{11}$ | $1.4 \times 10^{10}$ |
| BM MSC | 15PH05 P4 | third | 175 | 114 | $1.4 \times 10^{11}$ | $1.5 \times 10^{10}$ |
| BM MSC | 15PH05 P4(LPS) | third | 181 | 131 | $1.2 \times 10^{11}$ | $1.3 \times 10^{10}$ |
| CF | M1 P2 | | 161 | 114 | $1.9 \times 10^{11}$ | |
| CF | M1 P3 | | 165 | 131 | $3.2 \times 10^{11}$ | |
| CF | L1 P4 | | 170 | 115 | $2.6 \times 10^{11}$ | |
| CF | L1 P5 | | 182 | 113 | $3.5 \times 10^{11}$ | |
| CF | F1 P3 | | 160 | 128 | $2.4 \times 10^{11}$ | |
| CF | F1 P4 | | 158 | 146 | $2.3 \times 10^{11}$ | |
| Macrophage | | first | 159 | 116 | $6.5 \times 10^{11}$ | $3.3 \times 10^{12}$ |
| Corneal MSC | 2-224337 P5 | first | 149 | 119 | $1.1 \times 10^{12}$ | $6.1 \times 10^{10}$ |
| A375 Melanoma | | first | 153 | 121 | $5.8 \times 10^{12}$ | $2.8 \times 10^{11}$ |

*repeated analysis

Human cardiac fibroblasts were characterized by flow cytometry and compared to MSCs and dermal fibroblasts.

Figure 8:
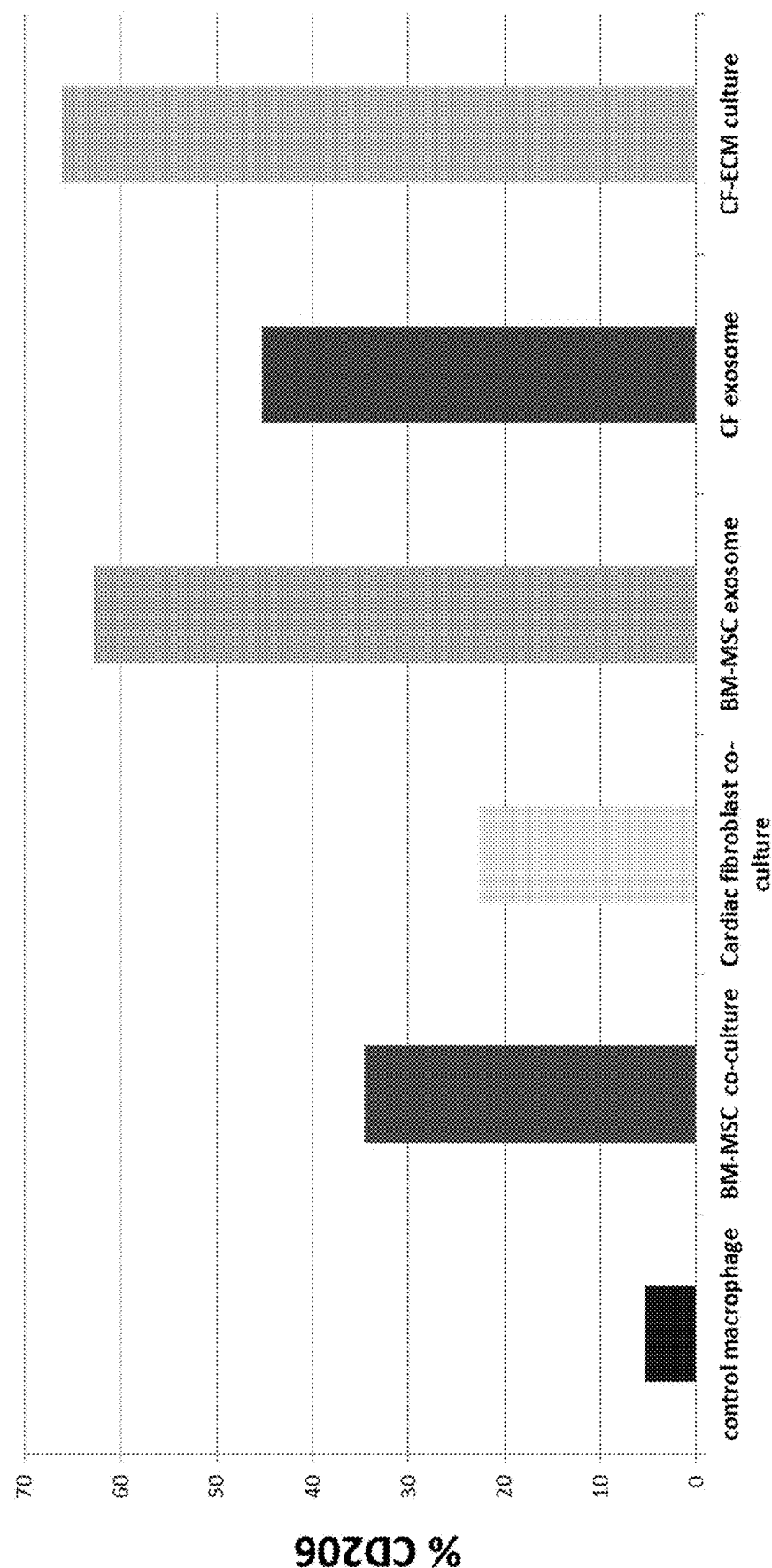
FIG. 8 shows the expression of CD206 in cardiac fibroblast extracellular matrix (CF-ECM) educated macrophages.

CD206, a specific marker for M2 macrophages was assayed by flow cytometry (FIG. 8) in uneducated macrophages (control) and compared to macrophages that were educated either by co-cultivation with cells, (MSCs (BM-MSC co-culture) or cardiac fibroblasts (cardiac fibroblasts co-culture)) with exosomes, (from either BM-MSCs (BM-MSC exosome) or CFs (CF exosome) or with extracted ECM from a CF culture (CF-ECM culture). Education using cells, exosomes, or ECMs increased the level of CD206 expression in the macrophages as determined based on percent cell expression as compared to the control macrophages. As expected, very low numbers of control macrophages expressed CD206. However, this expression increased from approximately 4 to 15 fold in the macrophages after education using either BM-MSC exosomes or ECMs from CFs. The results indicate that all three methods of education (CF-exosomes, BM-exosomes, and CF-ECM) could successfully educate the macrophages to an anti-inflammatory phenotype. Interestingly, the results under these conditions indicated that use of the extracellular factors, either with ECM or exosomes from either cell source, gave the strongest level of anti-inflammatory phenotype conversion in the macrophages.

Figure 9:
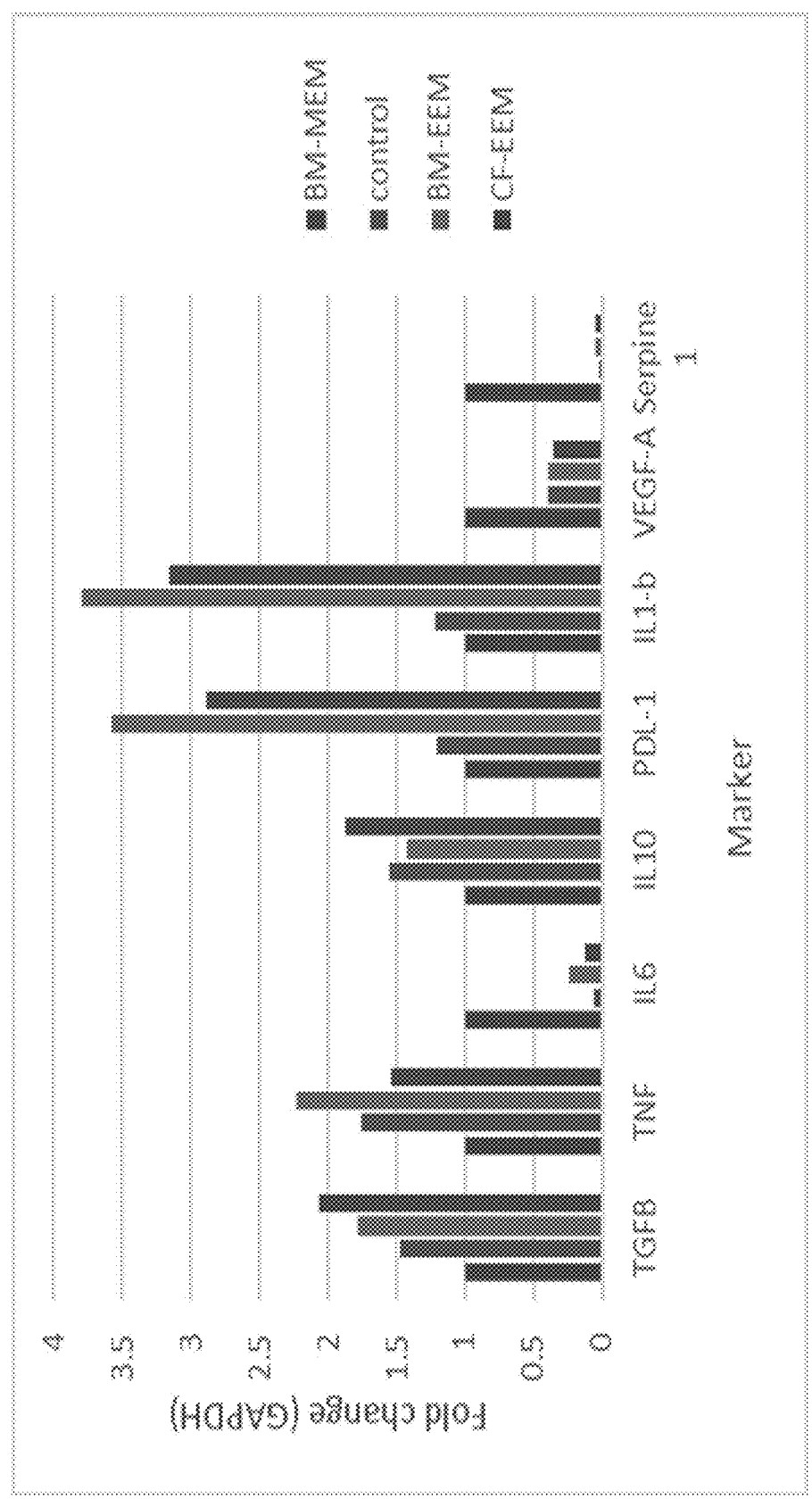
FIG. 9 depicts differences in gene expression of various cytokines, measured by qPCR.

Gene expression as determined by qPCR (FIG. 9) indicated that the expression profile of relevant genes involved in tissue repair and immune-suppression were different when comparing macrophages educated by co-cultivation with BM-MSCs (BM-MEM) to either un-educated macrophages (control) or macrophages educated using exosomes from BM-MSCs or CFs (BM-EEM, CF-EEMs, respectively). Certain anti-inflammatory cytokines (TGF-β, IL-10), immune-modulatory cytokines (IL-1b) and immunosuppressive molecules (PD-L1) involved in tissue repair were approximately 2 fold higher or more in both the BM-EEMs and the CF-EEMs as compared to the BM-MEMs. In contrast, other immune-modulatory cytokines (IL-6) and growth factors (VEGF-A, SERPINE-1) were at least 2-fold lower in both the BM and CF-EEMs. Overall the expression profiles for both the BM-EEMs and the CF-EEMs were similar to each other but distinct when compared to either the control macrophages or the BM-MEMs.

Figures 10A, 10B:
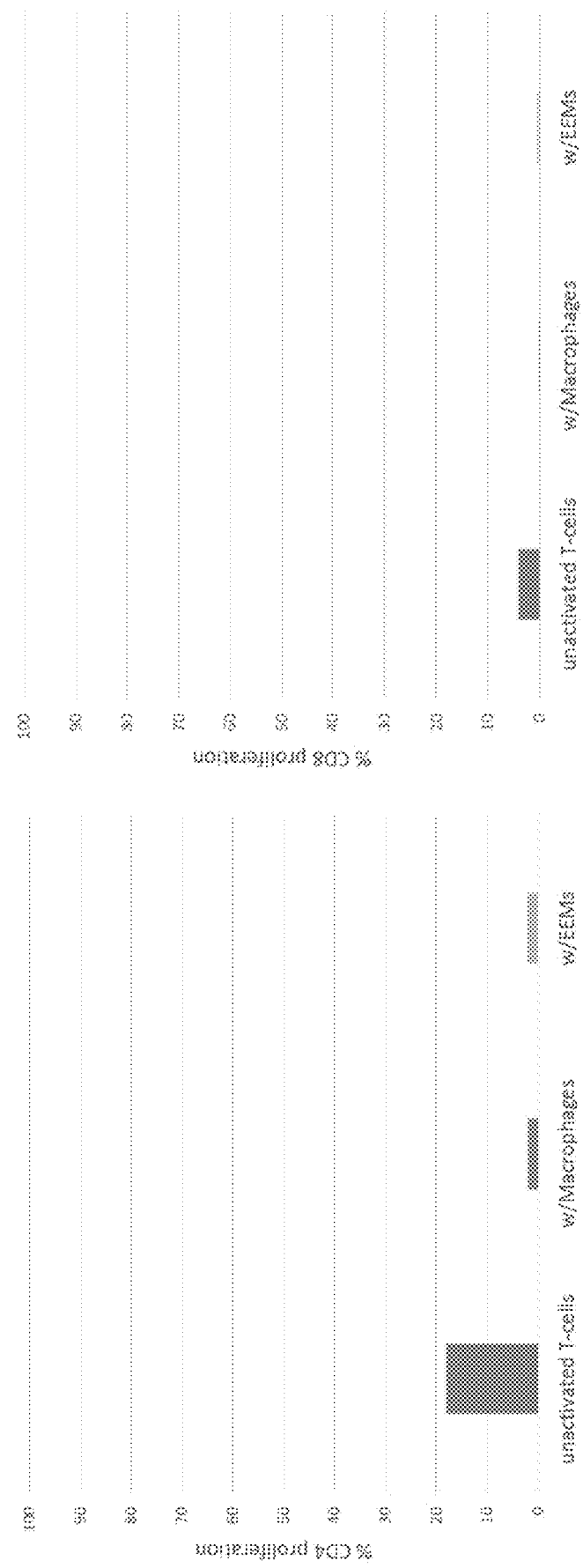
FIGS. 10A-10B depict the co-cultivation of unstimulated T-cells with either macrophages or BM-EEMs. The BM-EEMs do not cause activation and proliferation of T-cells.

The results shown in FIGS. 10A and 10B indicated that neither the uneducated macrophages nor the BM-EEMs, when mixed with the un-activated PBMCs (that is PBMCs without activating antibodies), could spontaneously induce proliferation in the T-cells in both (A)T-helper cells (CD4) or (B) T-cytotoxic cells (CD8) compared to their respective un-activated subtype (unactivated T-cells). This control experiment for immunosuppression needs to be determined first to rule out the possibility that the test cells themselves can stimulate proliferation in the absence of inducing antibodies. As hoped, no increased proliferation of either T-cell subtype occurred when co-cultured with macrophages or BM-EEMs when compared to the unactivated T cell controls.

Figure 11A:
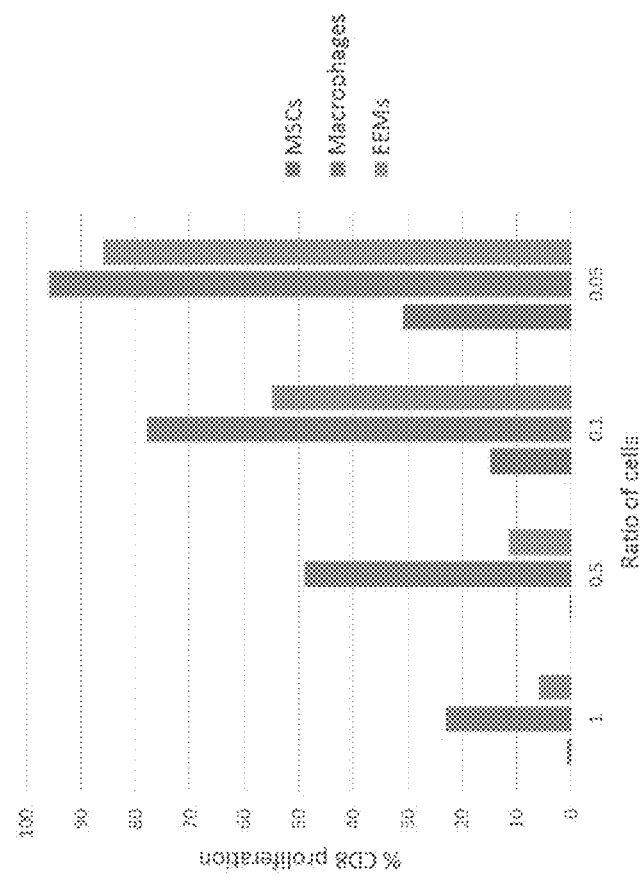
FIGS. 11A-11B depict in vitro functional assays of BM-EEMs. After T-cell activation, MSCs are known to suppress T-cell proliferation. BM-EEMs are more suppressive than uneducated macrophages.
Figure 11B:
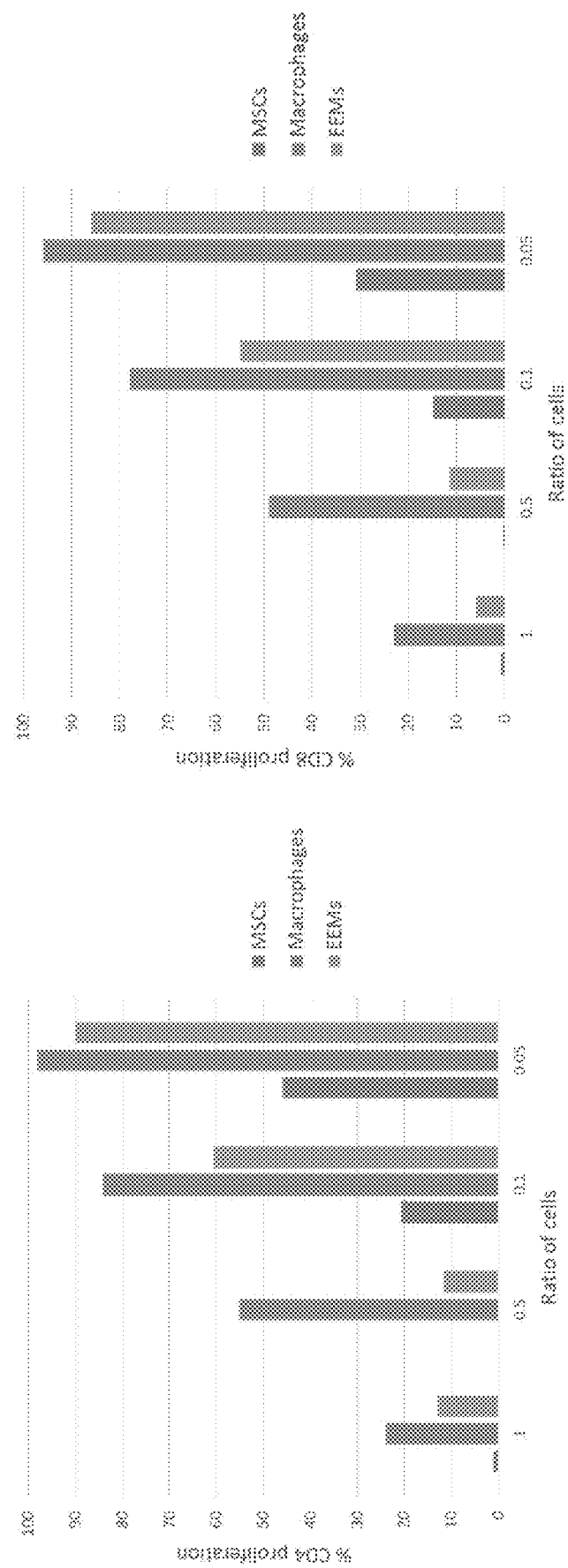
Figures 12A, 12B, 12C, 12D, 12E:
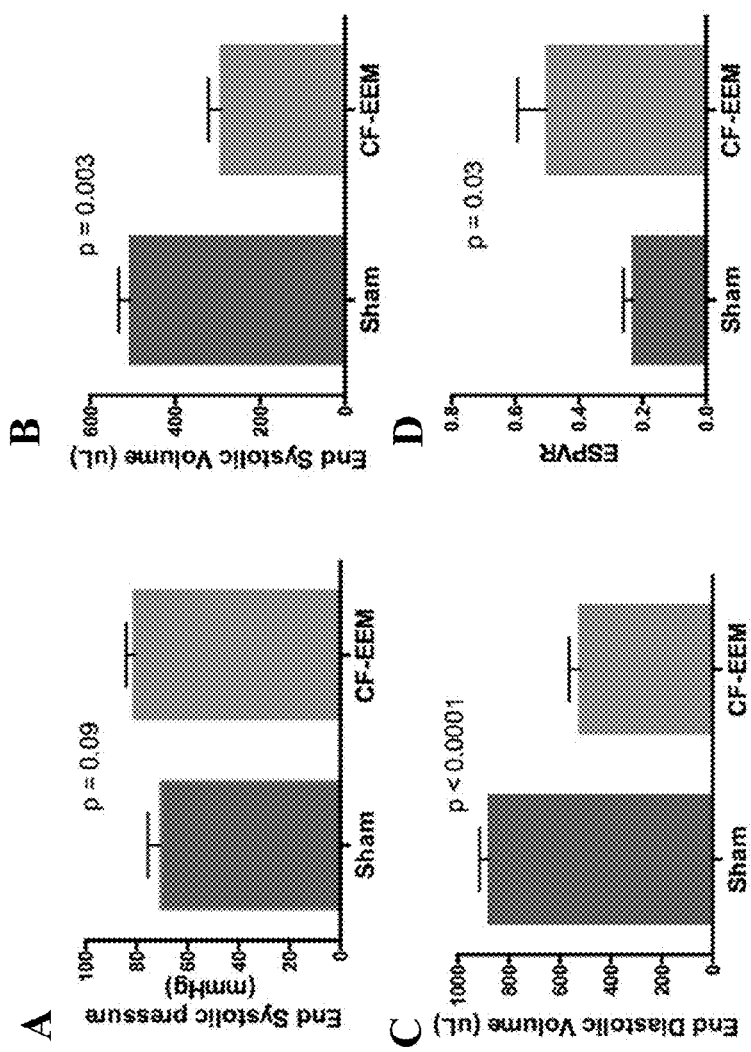
FIGS. 12A-12E show that CF-EEM delivered with cardiac extracellular matrix significantly improves cardiac function post myocardial infarction. Comparison between sham and CF-EEM/matrix treated rats post myocardial infarction demonstrates significant improvements in systolic pressures, reduced deleterious remodeling and increased cardiac contractility (measured as end systolic-pressure volume relationship, ESPVR). Significant angiogenesis was observed within the infarcted area (scar) in the treated animals as indicated by white arrows.
Figure 13:
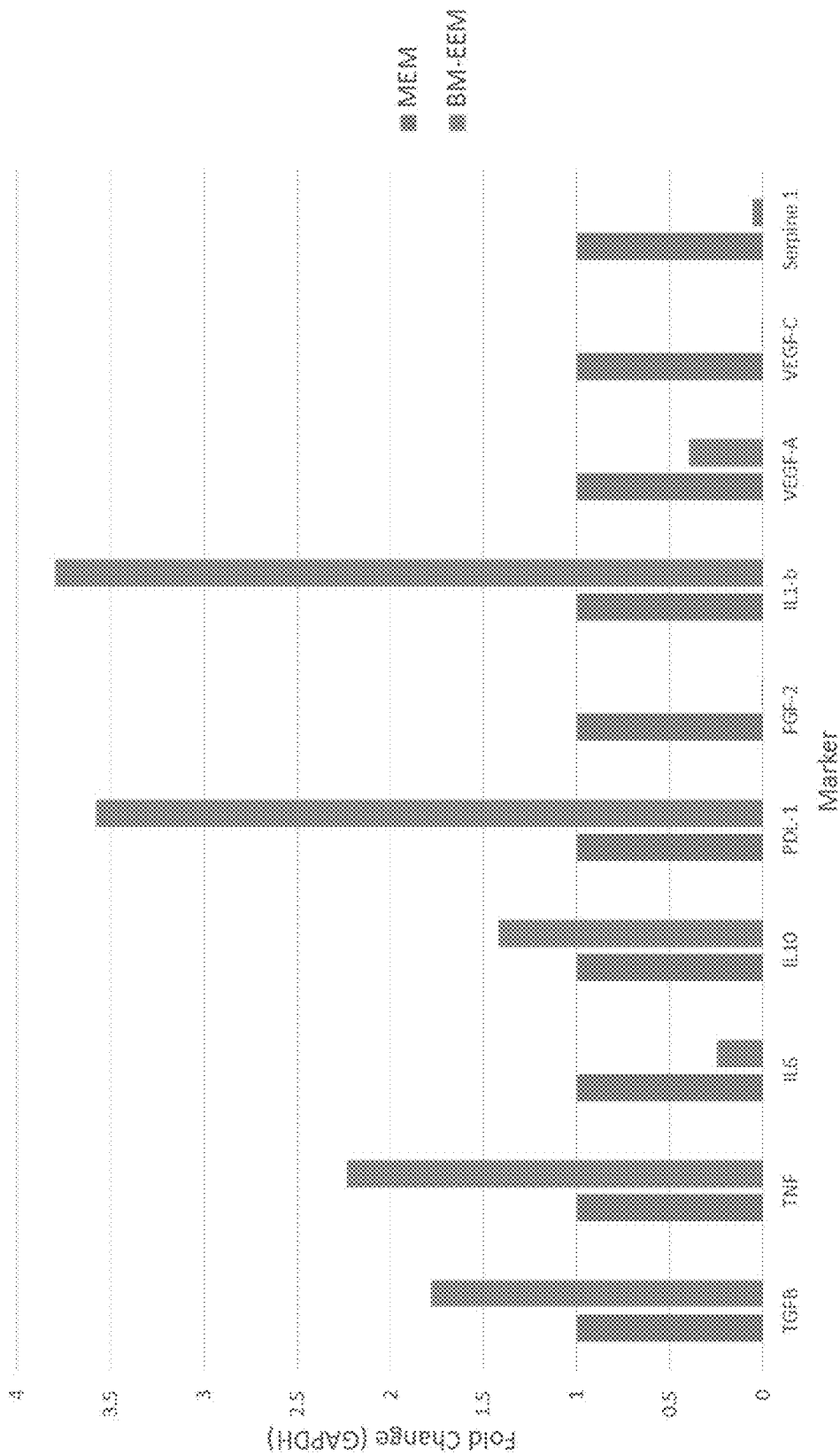
FIG. 13 compares qPCR gene expression in BM-MEMS vs BM-EEMs of various pro- and anti-inflammatory markers. To demonstrate the fold difference comparison between the two sets, the expression levels in the BM-MEM were set to a value of 1.
Figure 14:
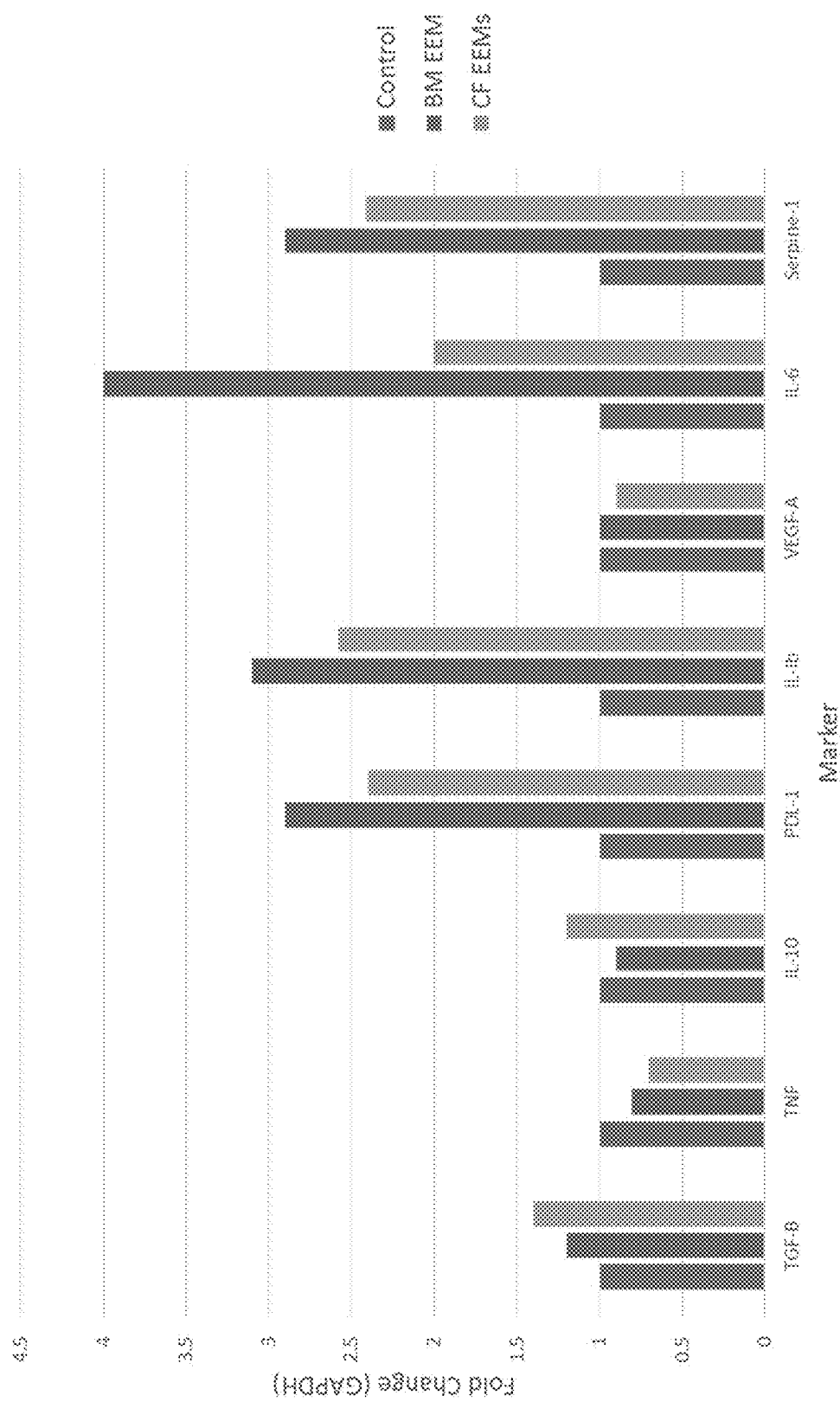
FIG. 14 compares qPCR gene expression in BM-EEMs, CF-EEMs and uneducated macrophages (control) of various pro- and anti-inflammatory markers. To demonstrate the fold difference comparison between all three sets, the expression levels in the control macrophages were set to a value of 1.

EEMs educated using exosomes isolated from BM-MSCs could effectively suppress antibody induced T-cell proliferation in both T-helper cells (A) and T-cytotoxic cells (B) subtypes when compared to uneducated control macrophages (Macrophages) (FIGS. 11A and 11B). Serving as a positive control for suppression, MSCs could effectively suppress the percent of T cell proliferation on both subtypes. A dose response at a PBMC to MSCs ratio of 1:1 to 1:0.05 is seen with complete suppression at 1:1 and approximately 30 to 35% proliferation (or essentially 65 to 70% growth suppression) at a ratio as low as 1:0.05. Much weaker suppression of both T-cell subtypes is seen using uneducated macrophages. Proliferation at about 50% (or 50% growth suppression) only occurs using a ratio of PBMCs to macrophages of 1:0.5 which then increases when using lower numbers of macrophages to PBMCs. In contrast, educated macrophages (EEMs) were stronger suppressors of proliferation of activated T-cells compared to uneducated macrophages. It is most apparent in both T-cell subtypes when comparing the ratio of PBMCs to macrophages or EEMs of 1:0.1; where there was about 80% proliferation in the T-cells co-cultivated with macrophages but only 15-20% with EEMs. Overall the results indicate that EEMs can effectively suppress proliferation in both T-cell subtypes in a dose dependent fashion and are better at T-cell suppression compared to uneducated macrophages.

Figure 18:
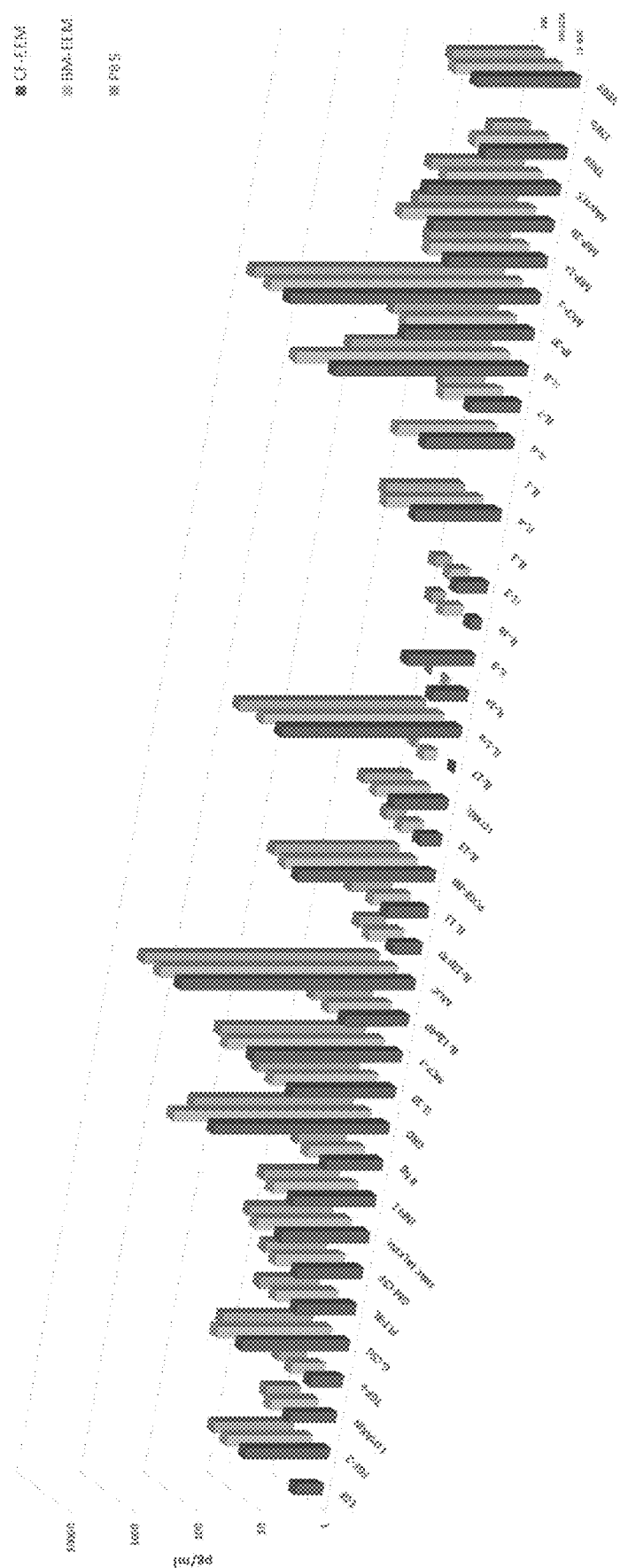
FIG. 18 shows CF-EEM secretome cytokine analysis characterization. CF-EEMs have a unique secretome compared to non-stimulated macrophages (PBS) and bone marrow EEMs (BM-EEM). CF-EEMs secrete EGF, compared to control macrophages (PBS) or BM-EEMS while BM-EEMs secrete significantly more GRO compared to CF-EEMs and control macrophages.
Figure 18:
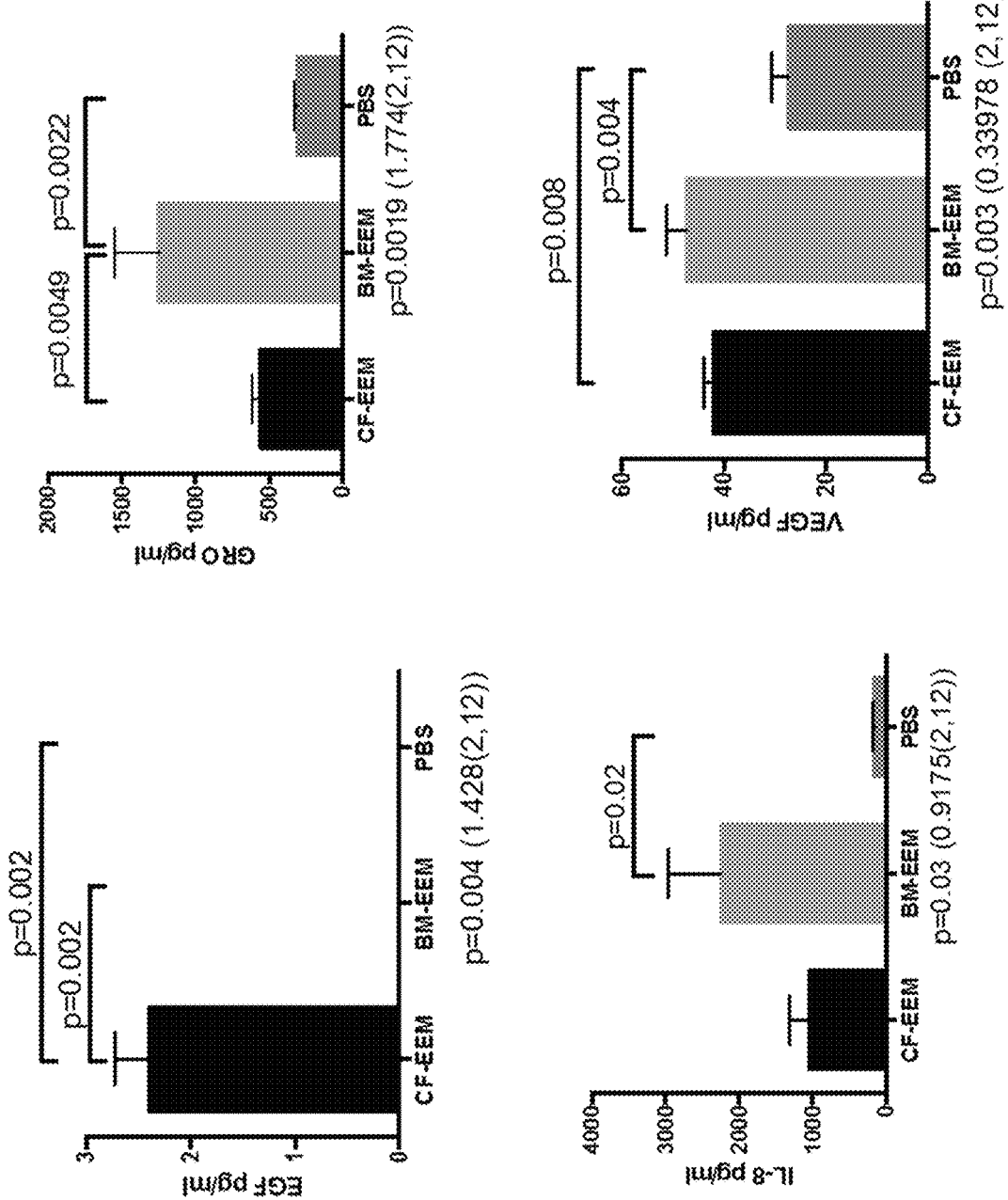

As shown in FIG. 18, CF-EEMs have a unique secretome compared to non-stimulated macrophages and bone marrow-MSC EEMs (BM-EEM). CF-EEMs secrete EGF, compared to control macrophages (PBS) or BM-EEMS while BM-EEMs secrete significantly more GRO compared to CF-EEMs and control macrophages. These results demonstrate that CF-EEMS are functionally distinct from BM-EEMS and control macrophages.

Figures 19A, 19B, 19C:
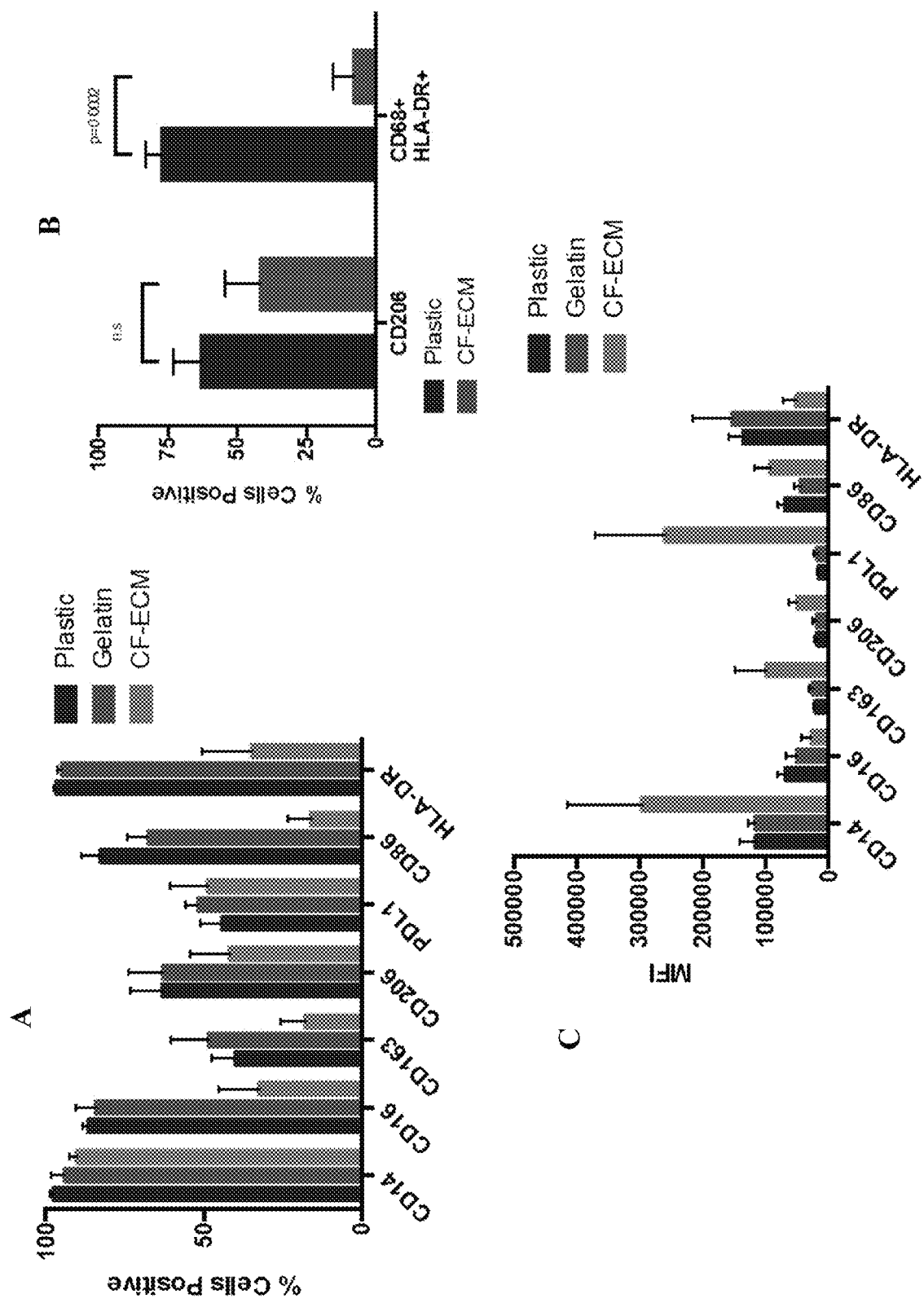
FIGS. 19A-19C show characterization of CF-ECM-EMs. Human macrophages were cultured on plastic, gelatin or CF-ECM for 3 days then removed from the surfaces and flow cytometry was used to analyze surface marker expression. Macrophages had a significantly higher expression (by mean fluorescent intensity) of CD14, CD163, CD206 and PDL (FIG. 19C). In addition, macrophages had significantly lower expression of inflammatory markers CD68 and HLA-DR (FIG. 19B). Macrophages cultured on cardiac fibroblast derived extracellular matrix (CF-ECM) (or CF-ECM-EMs) have a unique anti-inflammatory phenotype. CF-ECM-EMs have significantly lower expression of CD86 and HLA-DR, while PDL-1 expression is significantly increased (FIGS. 19A and 19C). PDL-1 is believed to play a major role in suppressing the immune system.

Macrophages cultured on cardiac fibroblast derived extracellular matrix (CF-ECM-EMs) have a unique anti-inflammatory phenotype. CF-ECM-EMs have significantly lower expression of CD86 and HLA-DR, while PDL-1 expression is significantly increased. PDL-1 is believed to play a major role in suppressing the immune system. As shown in FIG. 19, human macrophages were cultured on plastic, gelatin or CF-ECM for 3 days then removed from the surfaces and flow cytometry used to analyze surface marker expression. CF-ECM educated macrophages (CF-ECM-EM) had a significantly higher expression (by mean fluorescent intensity) of CD14, CD163, CD206 and PDL as compared to macrophages cultured on plastic or gelatin. In addition, CF-ECM-EM had significantly lower expression of inflammatory markers CD68 and HLA-DR as compared to macrophages cultured on plastic or gelatin. This data shows that CF-ECM education of $CD14^+$ cells generates macrophages which are phenotypically different than $CD^{14+}$ cells grown using commonly used methods for coating culture plates.

Cardiac fibroblast exosome-educated macrophages (CF-EEM) were transplanted into infarcted rat hearts using injectable cardiac fibroblast-derived extracellular matrix as a carrier. Animals treated with CF-EEMs showed a significant reduction in ventricular dilation (reduced end systolic and diastolic volumes) and a trend toward increased end systolic pressures (FIGS. 12A-12E) Most importantly, end systolic pressure volume relationship (ESPVR), the gold standard measurement for cardiac contractility, was significantly improved in CF-EEM treated animals. Taken together, CF-EEM treatment blunts deleterious post-MI cardiac remodeling and improves cardiac contractility.

In one embodiment a patient suffering from myocardial infarction or ischemic heart failure is treated as follows: 1) biopsy sufficient heart tissue from sick heart failure patients and expand the CFs into large quantities in culture, or isolate the CFs from healthy donor hearts that were not used for heart transplant instead of biopsy specimens from the patients themselves; (This cell harvesting method is currently used by a biotech company called Capricor Inc. (Beverly Hills, Calif.) backed by Johnson & Johnson (New Brunswick, N.J.) to derive "cardio-sphere-derived cells") ii) isolate CF-exosomes from the CFs; iii) harvest monocytes from the patient by performing leukapheresis or by any suitable method known in the art; iv) "educate" these monocytes with CF-exosomes to convert to cardio-specific anti-inflammatory macrophages using co-culture methods and; v) deliver the cardio-specific anti-inflammatory macrophages to the patient using minimally invasive, image guided transcatheter methods or other suitable methods known in the art. Leukapheresis is a highly efficient and safe procedure to obtain large quantities of mononuclear cells including monocytes and simply uses two IVs in each arm vein. Leukapheresis has been used for decades to harvest cells for hematopoietic reconstitution, and it also has been used safely for numerous advanced cardiovascular disease trials including those by Raval et al. A major advantage with our approach includes the ability to administer well-defined doses of CF exosome-educated macrophages (CF-EEM) to the patient.

Example 2 (Prophetic)

Figure 20:
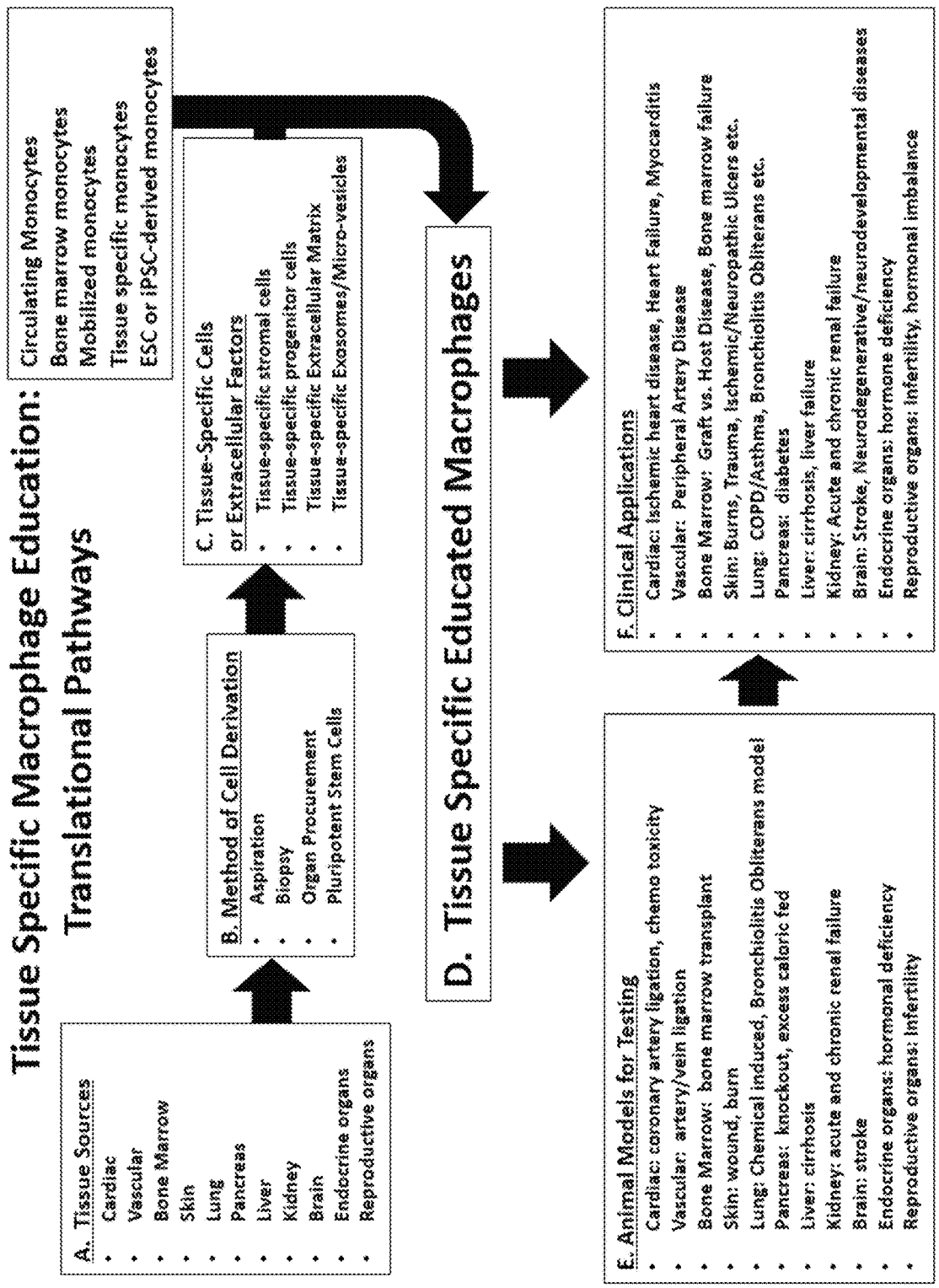
FIG. 20 represents a translation pathway of generating and using tissue-specific macrophages. Once a tissue source is identified (A), cells such as fibroblasts, tissue progenitor cells and others are harvested using biopsy or organ procurement or differentiated from pluripotent stem cells (B). Tissue-specific cells or extracellular factors, such as exosomes, micro-vesicles, and extracellular matrix, derived from the tissue-specific cells (C) are co-cultured with monocytes or macrophages to generate tissue-specific educated macrophages (D) that have pro-reparative, angiogenic, anti-inflammatory, and immunomodulatory phenotypes. Tissue-specific educated macrophages are expected to be phenotypically and functionally unique with unique cytokine, RNA, surface marker and functional expression. These tissue-specific educated macrophages can be delivered to a subject in need of treatment systemically or directly into injured tissues. Methods of delivery can include intravenous infusion, intravascular infusion, percutaneous injection, surgical injection, topical administration or any other delivery method described herein. Tissue-specific educated macrophages are expected to restore injured tissues as demonstrated in a variety of animal models (E) and clinical applications (F) in a tissue-specific manner.

Macrophages have an important role in tissue repair in response to ischemic, traumatic, inflammatory injury, and the normal aging process. In nature, alternatively activated, pro-regenerative macrophages are "switched on" or "polarized" from monocytes that reside in the bone marrow, circulation and tissues. However, in most cases, this innate repair response is inadequate as the tissue may be overwhelmed by the sheer magnitude of the tissue injury. We propose a novel therapeutic approach wherein pro-regenerative macrophages are manufactured in large quantities to then be delivered therapeutically. As depicted in FIG. 20, once a tissue source is identified (A), cells such as fibroblasts, tissue progenitor cells and others are harvested using aspiration, biopsy or organ procurement or differentiated from pluripotent stem cells, such as embryonic stem cells or induced pluripotent stem cells (B). Tissue-specific cells or extracellular factors, such as exosomes, micro-vesicles, and extracellular matrix, derived from the tissue-specific cells (C) are co-cultured with monocytes or macrophages to generate tissue-specific educated macrophages (D) that have pro-reparative, angiogenic, anti-inflammatory, and immunomodulatory phenotypes favorable to those specific tissues. Tissue-specific educated macrophages are expected to be phenotypically and functionally unique with unique cytokine, RNA, surface marker and functional expression. These tissue-specific educated macrophages can be delivered to a subject in need of treatment systemically or directly into injured tissues. Methods of delivery can include intravenous infusion, intravascular infusion, percutaneous injection, surgical injection, topical administration or any other delivery method described herein. Tissue-specific educated macrophages are expected to restore injured tissues as demonstrated in a variety of animal models (E) and clinical applications (F) in a tissue-specific manner.

Example 3 (Prophetic)

In this prophetic example, pulmonary fibroblasts, pneumocytes, or dust cells are obtained by biopsy or differentiation of pluripotent stem cells. Pulmonary fibroblasts, pneumocytes, or dust cells or their extracellular factors are co-cultured with circulating monocytes obtained through leukapheresis to generate lung-specific educated macrophages. These lung specific educated macrophages have a unique differential cytokine, growth factor, protein and RNA expression profile compared to traditional M1 or M2 macrophages or other tissue-specific macrophages. The lung-specific educated macrophages are administered to a subject, such as to recover or repair lung function in a rat inflammatory lung injury model and in humans with smoke inhalational lung injury, COPD, asthma, pulmonary fibrosis, or bronchiolitis obliterans.

Example 4 (Prophetic)

In this prophetic example, skin stromal cells such as keratinocytes or dermal fibroblasts are obtained by biopsy or differentiation of pluripotent stem cells. Skin cells or skin cell extracellular factors are co-cultured with circulating monocytes obtained through leukapheresis to generate skin specific educated macrophages. These skin-specific educated macrophages have a unique differential cytokine, growth factor, protein and RNA expression profile compared to traditional M1 or M2 macrophages or other tissue-specific macrophages. The skin-specific educated macrophages are administered to a subject, such as to heal a wound or burn in an animal skin injury model and in humans with burns, trauma, inflammatory skin disorders such as psoriasis, skin GVHD, systemic scleroderma, ischemic ulcers or neuropathic ulcers.

Example 5 (Prophetic)

In this prophetic example, pancreatic stromal cells, such as MSCs in the pancreas, pancreatic stromal or fibroblast cells, or pancreatic islet cells, are obtained by biopsy or differentiation of pluripotent stem cells. Pancreatic cells or pancreatic cell extracellular factors are co-cultured with circulating monocytes obtained through leukapheresis to generate pancreas-specific educated macrophages. These pancreas-specific educated macrophages have a unique differential cytokine, growth factor, protein and RNA expression profile compared to traditional M1 or M2 macrophages or other tissue-specific macrophages. The pancreas-specific educated macrophages are administered to a subject, such as to recover or repair pancreas function in an animal pancreas disease model, such as genetic knockouts or excess caloric intake models, and in humans with diabetes.

Example 6 (Prophetic)

In this prophetic example, liver cells, such as hepatocytes, Kuppfer cells, hepatic fibroblasts or MSCs, are obtained by biopsy or differentiation of pluripotent stem cells. Liver cells or liver cell extracellular factors are co-cultured with circulating monocytes obtained through leukapheresis to generate liver-specific educated macrophages. These liver-specific educated macrophages have a unique differential cytokine, growth factor, protein and RNA expression profile compared to traditional M1 or M2 macrophages or other tissue-specific macrophages. The liver-specific educated macrophages are administered to a subject, such as to recover or repair liver function in an animal model of cirrhosis and in humans with cirrhosis or liver failure.

Example 7 (Prophetic)

In this prophetic example, kidney cells, such as MSCs, fibroblasts, glomerular cells, tubular cells, podocytes or mesangial cells, are obtained by biopsy or differentiation of pluripotent stem cells. Kidney cells or kidney cell extracellular factors are co-cultured with circulating monocytes obtained through leukapheresis to generate kidney-specific educated macrophages. These kidney-specific educated macrophages have a unique differential cytokine, growth factor, protein and RNA expression profile compared to traditional M1 or M2 macrophages or other tissue-specific macrophages. The kidney-specific educated macrophages are administered to a subject, such as to recover or repair kidney function in an animal model of acute or chronic renal failure and in humans with acute or chronic renal failure, end stage renal disease, glomerulonephritis, and lupus nephritis.

Example 8 (Prophetic)

In this prophetic example, brain cells, such as glial cells, are obtained by biopsy or differentiation of pluripotent stem cells. Brain cells or brain cell extracellular factors are co-cultured with circulating monocytes obtained through leukapheresis to generate brain-specific educated macrophages. These brain-specific educated macrophages have a unique differential cytokine, growth factor, protein and RNA expression profile compared to traditional M1 or M2 macrophages or other tissue-specific macrophages. The brain-specific educated macrophages are administered to a subject, such as to recover or repair brain function in a rat or mouse stroke model and in humans with stroke, neurodegenerative diseases such as Alzheimer's, ALS, Parkinson's disease, or neurodevelopmental disease.

Example 9 (Prophetic)

In this prophetic example, cells from endocrine organs, such as fibroblasts or other stromal cells, are obtained by biopsy or differentiation of pluripotent stem cells. Endocrine fibroblasts or stromal cells, or their extracellular factors, are co-cultured with circulating monocytes obtained through leukapheresis to generate endocrine-specific educated macrophages. These endocrine-specific educated macrophages have a unique differential cytokine, growth factor, protein and RNA expression profile compared to traditional M1 or M2 macrophages or other tissue-specific macrophages. The endocrine-specific educated macrophages are administered to a subject, such as to recover or repair endocrine function in an animal model of hormone deficiency and in humans with hormone deficiency or inflammation of the endocrine organ.

Example 10 (Prophetic)

In this prophetic example, cells from reproductive organs, such as Leydig cells, MSCs and other stromal cells, are obtained by biopsy or differentiation of pluripotent stem cells. Cells from reproductive organs or extracellular factors derived therefrom are co-cultured with circulating monocytes obtained through leukapheresis to generate reproductive organ-specific educated macrophages. These reproductive organ-specific educated macrophages have a unique differential cytokine, growth factor, protein and RNA expression profile compared to traditional M1 or M2 macrophages or other tissue-specific macrophages. The reproductive organ-specific educated macrophages are administered to a subject, such as to recover or repair reproductive organ function in an animal model of infertility and in humans with infertility, hormonal imbalance, injury to a reproductive organ, menopause or normal aging reproductive hormonal deficiency such as low testosterone levels.

Example 11 (Prophetic)

In this prophetic example, vascular cells, such as pericytes or endothelial cells, are obtained by biopsy or differentiation of pluripotent stem cells. Pericytes, endothelial cells or their extracellular factors are co-cultured with circulating monocytes obtained through leukapheresis to generate vascular-specific educated macrophages. These vascular-specific educated macrophages have a unique differential cytokine, growth factor, protein and RNA expression profile compared to traditional M1 or M2 macrophages or other tissue-specific macrophages. The vascular-specific educated macrophages are administered to a subject, such as to recover or repair vascular function in an animal model of vein or artery ligation and in humans with peripheral artery disease.

REFERENCES

1. Go A S, Mozaffarian D, Roger V L, Benjamin E J, Berry J D, Blaha M J, Dai S, Ford E S, Fox C S, Franco S, Fullerton H J, Gillespie C, Hailpern S M, Heit J A, Howard V J, Huffman M D, Judd S E, Kissela B M, Kittner S J, Lackland D T, Lichtman J H, Lisabeth L D, Mackey R H, Magid D J, Marcus G M, Marelli A, Matchar D B, McGuire D K, Mohler E R, 3rd, Moy C S, Mussolino M E, Neumar R W, Nichol G, Pandey D K, Paynter N P, Reeves M J, Sorlie P D, Stein J, Towfighi A, Turan T N, Virani S S, Wong N D, Woo D, Turner M B. Heart disease and stroke statistics—2014 update: A report from the american heart association. *Circulation.* 2014; 129:e28-e292
2. Menasche P, Vanneaux V. Stem cells for the treatment of heart failure. *Curr Res Transl Med.* 2016; 64:97-106
3. Huang P, Tian X, Li Q, Yang Y. New strategies for improving stem cell therapy in ischemic heart disease. *Heart Fail Rev.* 2016; 21:737-752
4. Zwetsloot P P, Vegh A M, Jansen of Lorkeers S J, van Hout G P, Currie G L, Sena E S, Gremmels H, Buikema J W, Goumans M J, Macleod M R, Doevendans P A, Chamuleau S A, Sluijter J P. Cardiac stem cell treatment in myocardial infarction: A systematic review and meta-analysis of preclinical studies. *Circ Res.* 2016; 118:1223-1232
5. Suzuki G. Translational research of adult stem cell therapy. *World J Cardiol.* 2015; 7:707-718
6. Raval A N. Therapeutic potential of adult progenitor cells in the management of chronic myocardial ischemia. *American journal of cardiovascular drugs: drugs, devices, and other interventions.* 2008; 8:315-326
7. Raval A N, Kamp T J, Hogle L F. Cellular therapies for heart disease: Unveiling the ethical and public policy challenges. *Journal of molecular and cellular cardiology.* 2008; 45:593-601
8. Ibrahim A G, Cheng K, Marban E. Exosomes as critical agents of cardiac regeneration triggered by cell therapy. *Stem Cell Reports.* 2014; 2:606-619
9. Prathipati P, Nandi S S, Mishra P K. Stem cell-derived exosomes, autophagy, extracellular matrix turnover, and mirnas in cardiac regeneration during stem cell therapy. *Stem Cell Rev.* 2016
10. Kishore R, Khan M. More than tiny sacks: Stem cell exosomes as cell-free modality for cardiac repair. *Circ Res.* 2016; 118:330-343
11. Kim J, Hematti P. Mesenchymal stem cell-educated macrophages: A novel type of alternatively activated macrophages. *Experimental hematology.* 2009; 37:1445-1453
12. Asimakopoulos F, Kim J, Denu R A, Hope C, Jensen J L, Ollar S J, Hebron E, Flanagan C, Callander N, Hematti P. Macrophages in multiple myeloma: Emerging concepts and therapeutic implications. *Leuk Lymphoma.* 2013; 54:2112-2121
13. Bashir S, Sharma Y, Elahi A, Khan F. Macrophage polarization: The link between inflammation and related diseases. *Inflamm Res.* 2016; 65:1-11

14. Fujiu K, Wang J, Nagai R. Cardioprotective function of cardiac macrophages. *Cardiovascular research*. 2014; 102:232-239
15. Chakravarty T, Makkar R R, Ascheim D, Traverse J H, Schatz R, DeMaria A, Francis G S, Povsic T J, Smith R, Lima J A, Pogoda J M, Marban L, Henry T D. Allogeneic heart stem cells to achieve myocardial regeneration (allstar) trial: Rationale & design. *Cell transplantation*. 2016
16. Tomkowiak M T, Klein A J, Vigen K K, Hacker T A, Speidel M A, VanLysel M S, Raval A N. Targeted transendocardial therapeutic delivery guided by mri-x-ray image fusion. *Catheterization and cardiovascular interventions: official journal of the Society for Cardiac Angiography & Interventions*. 2011; 78:468-478
17. Schmuck E G, Koch J M, Hacker T A, Hatt C R, Tomkowiak M T, Vigen K K, Hendren N, Leitzke C, Zhao Y Q, Li Z, Centanni J M, Hei D J, Schwahn D, Kim J, Hematti P, Raval A N. Intravenous followed by x-ray fused with mri-guided transendocardial mesenchymal stem cell injection improves contractility reserve in a swine model of myocardial infarction. *Journal of cardiovascular translational research*. 2015; 8:438-448
18. de Silva R, Gutierrez L, Raval A, McVeigh E, Ozturk C, Lederman R. X-ray fused with magnetic resonance imaging (xfm) to target endomyocardial injections: Validation in a swine model of myocardial infarction. *Circulation*. 2006; 114:2342-2350
19. Hatt C R, Jain A K, Parthasarathy V, Lang A, Raval A N. Mri-3d ultrasound-x-ray image fusion with electromagnetic tracking for transendocardial therapeutic injections: In-vitro validation and in-vivo feasibility. *Comput Med Imaging Graph*. 2013; 37:162-173
20. Losordo D W, Schatz R A, White C J, Udelson J E, Veereshwarayya V, Durgin M, Poh K K, Weinstein R, Kearney M, Chaudhry M, Burg A, Eaton L, Heyd L, Thorne T, Shturman L, Hoffmeister P, Story K, Zak V, Dowling D, Traverse J H, Olson R E, Flanagan J, Sodano D, Murayama T, Kawamoto A, Kusano K F, Wollins J, Welt F, Shah P, Soukas P, Asahara T, Henry T D. Intramyocardial transplantation of autologous cd34+ stem cells for intractable angina: A phase i/iia double-blind, randomized controlled trial. *Circulation*. 2007; 115:3165-3172
21. Losordo D W, Henry T D, Davidson C, Sup Lee J, Costa M A, Bass T, Mendelsohn F, Fortuin F D, Pepine C J, Traverse J H, Amrani D, Ewenstein B M, Riedel N, Story K, Barker K, Povsic T J, Harrington R A, Schatz R A. Intramyocardial, autologous cd34+ cell therapy for refractory angina. *Circulation research*. 2011; 109:428-436
22. Losordo D W, Kibbe M R, Mendelsohn F, Marston W, Driver V R, Sharafuddin M, Teodorescu V, Wiechmann B N, Thompson C, Kraiss L, Carman T, Dohad S, Huang P, Junge C E, Story K, Weistroffer T, Thorne T M, Millay M, Runyon J P, Schainfeld R. A randomized, controlled pilot study of autologous cd34+ cell therapy for critical limb ischemia. *Circulation. Cardiovascular interventions*. 2012; 5:821-830
23. Povsic T J, Henry T D, Traverse J H, Fortuin F D, Schaer G L, Kereiakes D J, Schatz R A, Zeiher A M, White C J, Stewart D J, Jolicoeur E M, Bass T, Henderson D A, Dignacco P, Gu Z, Al-Khalidi H R, Junge C, Nada A, Hunt A S, Losordo D W. The renew trial: Efficacy and safety of intramyocardial autologous cd34(+) cell administration in patients with refractory angina. *JACC. Cardiovascular interventions*. 2016; 9:1576-1585
24. Kovacic J C, Macdonald P, Feneley M P, Muller D W, Freund J, Dodds A, Milliken S, Tao H, Itescu S, Moore J, Ma D, Graham R M. Safety and efficacy of consecutive cycles of granulocyte-colony stimulating factor, and an intracoronary cd133+ cell infusion in patients with chronic refractory ischemic heart disease: The g-csf in angina patients with ihd to stimulate neovascularization (gain i) trial. *American heart journal*. 2008; 156:954-963
25. Raval A N, Schmuck E G, Tefera G, Leitzke C, Ark C V, Hei D, Centanni J M, de Silva R, Koch J, Chappell R G, Hematti P. Bilateral administration of autologous cd133+ cells in ambulatory patients with refractory critical limb ischemia: Lessons learned from a pilot randomized, double-blind, placebo-controlled trial. *Cytotherapy*. 2014; 16:1720-1732
26. Lalit P A, Salick M R, Nelson D O, Squirrell J M, Shafer C M, Patel N G, Saeed I, Schmuck E G, Markandeya Y S, Wong R, Lea M R, Eliceiri K W, Hacker T A, Crone W C, Kyba M, Garry D J, Stewart R, Thomson J A, Downs K M, Lyons G E, Kamp T J. Lineage reprogramming of fibroblasts into proliferative induced cardiac progenitor cells by defined factors. *Cell Stem Cell*. 2016; 18:354-367
27. Mozaffarian D, Benjamin E J, Go A S, Arnett D K, Blaha M J, Cushman M, Das S R, de Ferranti S, Despres J P, Fullerton H J, Howard V J, Huffman M D, Isasi C R, Jimenez M C, Judd S E, Kissela B M, Lichtman J H, Lisabeth L D, Liu S, Mackey R H, Magid D J, McGuire D K, Mohler E R, 3rd, Moy C S, Muntner P, Mussolino M E, Nasir K, Neumar R W, Nichol G, Palaniappan L, Pandey D K, Reeves M J, Rodriguez C J, Rosamond W, Sorlie P D, Stein J, Towfighi A, Turan T N, Virani S S, Woo D, Yeh R W, Turner M B. Heart disease and stroke statistics—2016 update: A report from the american heart association. *Circulation*. 2016; 133:e38-360
28. Schmuck E G, Mulligan J D, Ertel R L, Kouris N A, Ogle B M, Raval A N, Saupe K W. Cardiac fibroblast-derived 3d extracellular matrix seeded with mesenchymal stem cells as a novel device to transfer cells to the ischemic myocardium. *Cardiovascular Engineering and Technology*. 2014; 5:119-131
29. Lalit P A, Salick M R, Nelson D O, Squirrell J M, Shafer C M, Patel N G, Saeed I, Schmuck E G, Markandeya Y S, Wong R, Lea M R, Eliceiri K W, Hacker T A, Crone W C, Kyba M, Garry D J, Stewart R, Thomson J A, Downs K M, Lyons G E, Kamp T J. Lineage reprogramming of fibroblasts into proliferative induced cardiac progenitor cells by defined factors. *Cell Stem Cell*. 2016; 18:354-367
30. Ye L, Chang Y H, Xiong Q, Zhang P, Zhang L, Somasundaram P, Lepley M, Swingen C, Su L, Wendel J S, Guo J, Jang A, Rosenbush D, Greder L, Dutton J R, Zhang J, Kamp T J, Kaufman D S, Ge Y. Cardiac repair in a porcine model of acute myocardial infarction with human induced pluripotent stem cell-derived cardiovascular cells. *Cell Stem Cell*. 2014; 15:750-761
31. Zhang J, Klos M, Wilson G F, Herman A M, Lian X, Raval K K, Barron M R, Hou L, Soerens A G, Yu J, Palecek S P, Lyons G E, Thomson J A, Herron T J, Jalife J, Kamp T J. Extracellular matrix promotes highly efficient cardiac differentiation of human pluripotent stem cells: The matrix sandwich method. *Circulation research*. 2012; 111:1125-1136
32. Lian X, Hsiao C, Wilson G, Zhu K, Hazeltine L B, Azarin S M, Raval K K, Zhang J, Kamp T J, Palecek S P. Robust cardiomyocyte differentiation from human pluripotent stem cells via temporal modulation of canonical wnt signaling. *Proceedings of the National Academy of Sciences of the United States of America*. 2012; 109: E1848-1857

33. Zhang J, Wilson G F, Soerens A G, Koonce C H, Yu J, Palecek S P, Thomson J A, Kamp T J. Functional cardiomyocytes derived from human induced pluripotent stem cells. *Circulation research.* 2009; 104:e30-41
34. Warrick J W, Young E W, Schmuck E G, Saupe K W, Beebe D J. High-content adhesion assay to address limited cell samples. *Integr Biol (Camb).* 2013; 5:720-727
35. Bloom D D, Centanni D H, Bhatia N, Emler C A, Drier D, Leverson G E, McKenna D H, Gee A P, Lindblad R, Hei D J, Hematti P. A Reproducible Immunopotency Assay to Measure Mesenchymal Stromal Cell Mediated T cell Suppression. Department Cytotherapy. 2015 February; 17(2): 140-151.

We claim:

1. A human population of CD163 low, CD206 high, CD16 low, PD-L1 high, PD-L2 high, TGF-β high, TNF-α low, IL-6 high anti-inflammatory macrophages as compared to uneducated macrophages, wherein the population of anti-inflammatory macrophages are produced by a method comprising co-culturing a population of isolated CD14+ cells with exosomes derived from cardiac fibroblasts in vitro until the population of isolated CD14+ cells acquire an anti-inflammatory macrophage phenotype, wherein the population of anti-inflammatory macrophages comprises CD163 low, CD206 high, CD low, PD-L1 high, PD-L2 high, TGF-β high, TNF-α low, IL-6 high, IL-10 high, IL-1b high, and Serpine-1 high cardiac fibroblast exosome educated macrophages (CF-EEM) macrophages as compared to uneducated macrophages.

2. A composition comprising:
    the population of macrophages of claim 1; and
    a pharmaceutically-acceptable carrier.

3. The composition of claim 2, wherein the carrier is selected from the group consisting of liquid, oil, lotion, salve, cream, foam, gel, paste, powder, film, and hydrogel.

4. The composition of claim 2, wherein the carrier is an injectable cardiac fibroblast-derived extracellular matrix (CF-ECM).

5. The composition of claim 4, wherein the CF-ECM additionally comprises cardiac fibroblast derived exosomes.

6. A method for generating an anti-inflammatory macrophage of claim 1, the method comprising the step of:
    co-culturing a population of isolated CD14+ cells with exosomes derived from cardiac fibroblasts in vitro until the population of isolated CD14+ cells acquire an anti-inflammatory macrophage phenotype, wherein the population of anti-inflammatory macrophages comprises CD163 low, CD206 high, CD16 low, PD-L1 high, PD-L2 high, TGF-β high, TNF-α low, IL-6 high, IL-10 high, IL-1b high, and Serpine-1 high cardiac fibroblast exosome educated macrophages (CF-EEM) as compared to uneducated macrophages.

7. The method of claim 6, wherein the CD14+ cell is a monocyte.

8. A method of treatment to alleviate a condition in a subject in need thereof, the method comprising the step of: administering to the subject the population of macrophages of claim 1, wherein the condition is a cardiovascular disease.

9. The method of claim 8, wherein the population of macrophages is administered by injection.

10. The method of claim 8, wherein the condition is ischemic heart failure.

11. The method of claim 10, wherein the macrophages are administered by injection with a pharmaceutically-acceptable carrier.

12. The method of claim 11, wherein the carrier is an injectable cardiac fibroblast-derived extracellular matrix.

* * * * *